US005208018A

United States Patent [19]

Gough

[11] Patent Number: 5,208,018

[45] Date of Patent: May 4, 1993

[54] TREATMENT OF CACHEXIA WITH INTERLEUKIN 2

[75] Inventor: David B. Gough, Galway, Ireland

[73] Assignee: Brigham and Women's Hospital, Boston, Mass.

[21] Appl. No.: 672,703

[22] Filed: Mar. 19, 1991

Related U.S. Application Data

[63] Continuation-in-part of Ser. No. 495,049, Mar. 19, 1990.

[51] Int. Cl.[5] ...................... A61K 37/02; A61K 45/05

[52] U.S. Cl. ................................................ 424/85.2

[58] Field of Search ...................................... 424/85.2

[56] References Cited

FOREIGN PATENT DOCUMENTS 0092163 10/1983 European Pat. Off. .
0118977 9/1984 European Pat. Off. .

OTHER PUBLICATIONS

Fearon et al., *Ann. Surgery* 208(1):1-5 (1988).
Kern et al., *Journal of Parenteral and Enteral Nutrition* 12(3):286-298 (1988).
Beutler et al., *Ann. Rev. Immunol.* 7:625-655 (1989).
Balkwill et al., *The Lancet*, pp. 1229-1232 (Nov. 28, 1987).
Remick et al., *Laboratory Investigation* 56(6):583-590 (1987).
Michie et al., *Surgery* 104(2):280-286 (1988).
Michie et al., *Ann. Surg.* 208(4):493-504 (1988).
Michie et al., *Ann. Surg.* 209(1):19-24 (1989).
Fraker et al., *Amer. J. Physiol.* 256:E725-E731 (1989).
Monson et al., *Br. J. Surg.* 73:483-486 (1986).
Gough et al., *Surgery* 104(2):292-300 (1988).
Rosenberg et al., *J. Exp. Med.* 161:1169-1188 (1985).
Nedwin et al., *The Journal of Immunology* 135(4):2492-2497 (1985).
Rosenberg et al., *The New England Journal of Medicine* 313(23):1485-1492 (1985).
Rosenberg, Steven A., *Ann. Surg.* 208(2):121-135 (1988).
Tracey et al., *Surgery, Gynecology & Obstetrics* 164:415-422 (1987).
Oliff et al., *Cell* 50:555-563 (1987).

*Primary Examiner*—Merrell C. Cashion, Jr.
*Assistant Examiner*—Choon P. Koh
*Attorney, Agent, or Firm*—Sterne, Kessler, Goldstein & Fox

[57] ABSTRACT

A method of treating cachexia associated with cancer, infectious diseases, or catabolic disorders which comprises administration of an effective amount of interleukin 2 is disclosed.

20 Claims, 21 Drawing Sheets

FIG. 4A
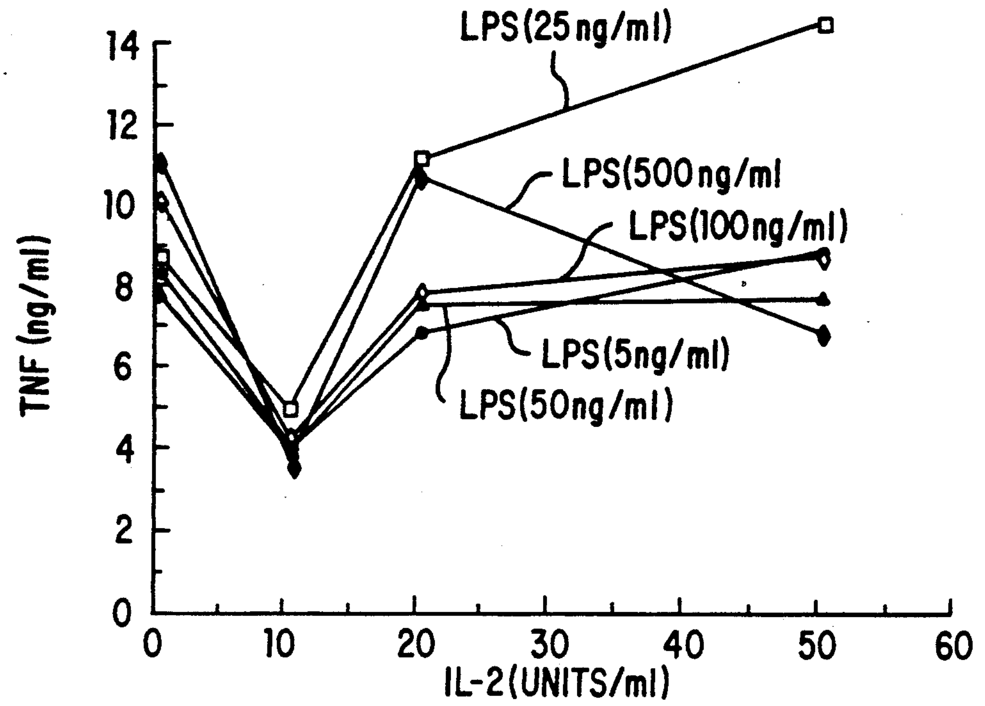
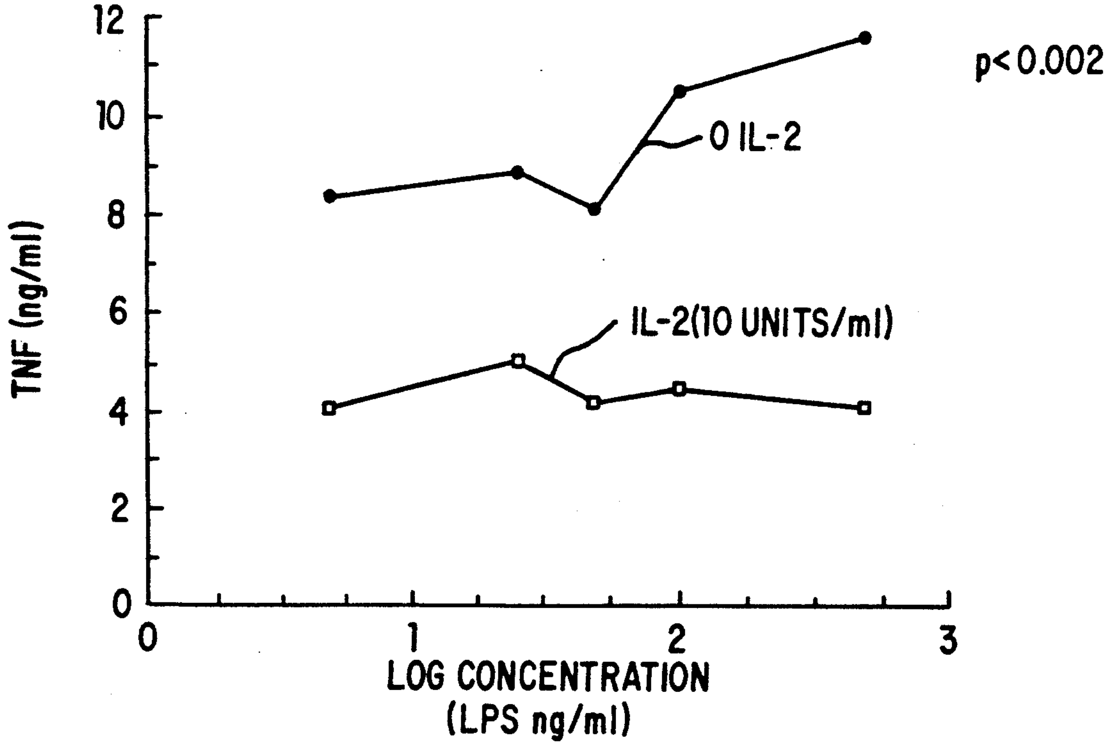
FIG. 4B

FIG. 5A
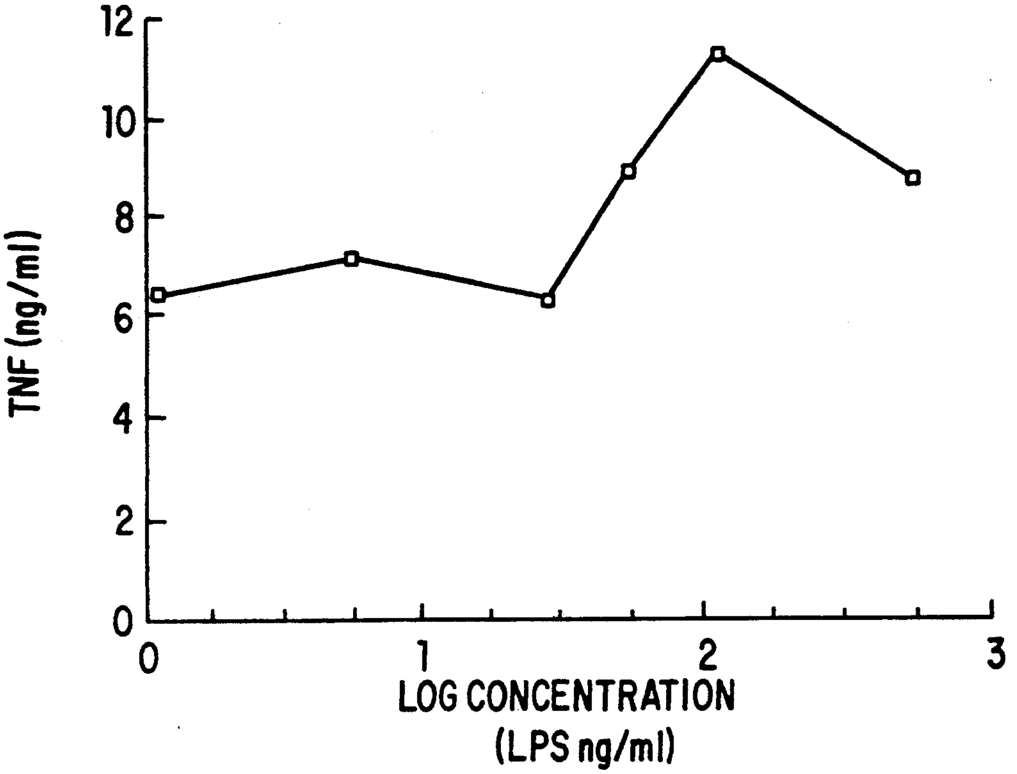
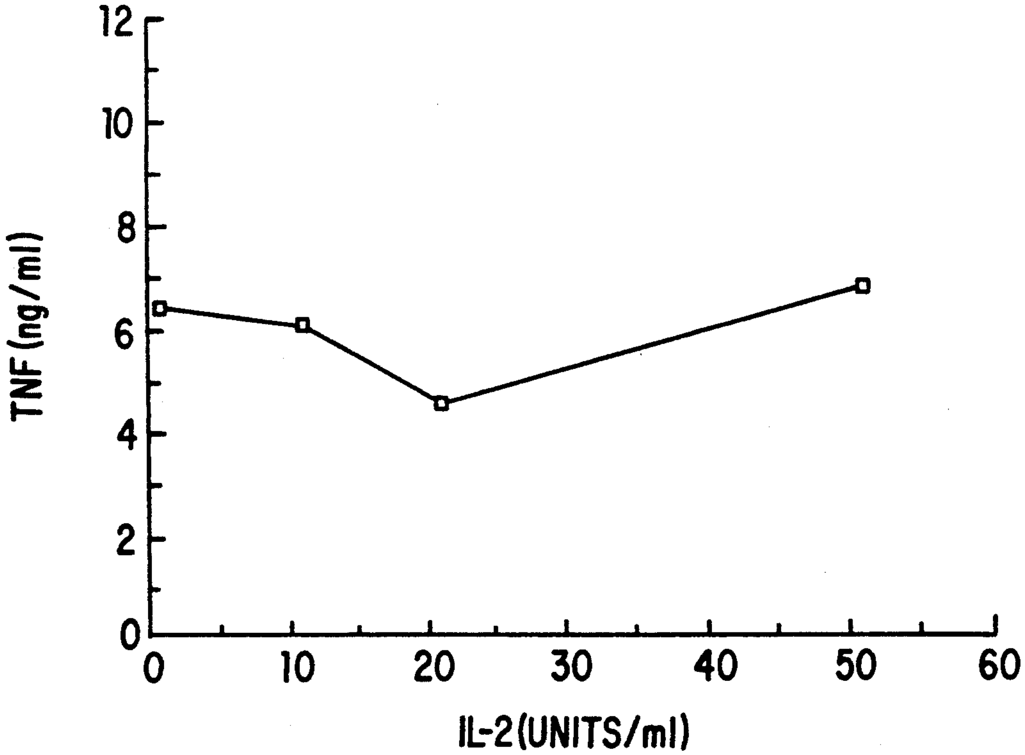
FIG. 5B

TREATMENT OF CACHEXIA WITH INTERLEUKIN 2

RELATED APPLICATION

This application is a continuation-in-part of U.S. application Ser. No. 07/495,049 filed on Mar. 19, 1990.

BACKGROUND OF THE INVENTION

1. Field of the Invention

The invention relates to the use of interleukin 2 to treat cachexia associated with cancer, infectious disease, and other catabolic states.

2. Description of the Background Art

One of the major and most characteristic problems seen in cancer patients is weight loss, usually associated with anorexia. The extensive wasting which results is known as "cachexia." The causes for this commonly observed and often life-limiting disturbance remain to be determined, even though many contributing factors have been identified Mendelsohn, J., *Principles of Neoplasta* in Harrison's PRINCIPLES OF INTERNAL MEDICINE, 11th Ed., (Braunwald et al., Eds.) McGraw-Hill Book Co., New York, 1987, Chap. 78, pp. 421–431). The cachectic state is associated with significant morbidity and is responsible for the majority of cancer mortality, despite advances in nutritional support. (Fearon, K. C. H. et al., *Ann. Surg.* 208:1–5 (1988)).

In a review, Kern, K. A. et al. (*J. Parent. Enter. Nutr.* 12:286–298 (1988)) described cancer cachexia as a syndrome which includes progressive weight loss, anorexia, and persistent erosion of body mass in response to a malignant growth. The fundamental physiological derangement as said to be a decline in food intake relative to energy expenditure. Insulin therapy has been proposed as one way to preserve host composition. However, to date, no successful form of therapy has been found.

A number of studies have suggested that a molecule known alternatively as tumor necrosis factor (TNF), cachectin, or TNF/cachectin, is an important mediator of cachexia in cancer, infectious disease, and other catabolic states. The biology and chemistry of TNF has been reviewed extensively in recent years (Beutler, B. et al., *Nature* 320:584–588 (1986); Parasitol. Today 3:345–346 (1987); *Ann Rev. Immunol.* 7:625–655 (1989); Le, J. et al., *Lab. Invest.* 56:234–248 (1987); Old, L. J., *Science* 230:630–632 (1985); Nature 326:330–331 (1987); Palladino, M. A., *J. Natl Canc. Inst.* 81:474–475 (1989); Playfair, J. H. L. et al., *Immunol. Today* 5:165–166 (1984); Ruddle, N. H., *Immunol. Today* 8:129–130 (1987); Tracey, K. J. et al., *J. Infec. Dis.* 157:413–420 (1988 March). Leading experts in the area have recently concluded that our understanding of the role of TNF is too shallow to allow a precise assessment of conditions under which its administration or removal would prove to be of benefit (Beutler, B. et al., *Ann Rev. Immunol.* 7:625–655 (1989)).

TNF was initially discovered on the basis of its ability to kill tumor cells and shrink tumor mass (hence the name "tumor necrosis factor"). TNF has therefore been tested as an anti-tumor therapeutic agent in pre-clinical trials (see, for example, Nishimura, T. et al., *Int. J. Canc.* 40:255–261 (1987); Zimmerman, R. J. et al., *J. Natl. Canc. Inst.* 81:227–231 (1989)) and in clinical studies (see below). The paradoxical discovery that some of the major life-threatening clinical sequelae of cancer are mediated, at least in part, by the very molecule that may be important in host defense against cancer has cast a pall over this area of research. (See, for example, Balkwill, F. et al., *Lancet* 1229–1232 (1987).

The Endotoxin-TNF Connection

It has been known for some time that in bacterial infection, sepsis and critical illness, bacterial lipopolysaccharides (LPS), or endotoxins, are responsible for many of the pathophysiological manifestations, including fever, malaise, anorexia, and cachexia. More recently, it was observed that TNF can mimic many endotoxin effects, leading to the suggestion that TNF, and related cytokines derived from cells of the macrophage/monocyte family, are central mediators responsible for the clinical manifestations of the illness.

Endotoxin is a potent monocyte/macrophate activator which stimulates the production and secretion of TNF (Kornbluth, S. K. et al., *J. Immunol.* 137:2585–2591 (1986)) and other cytokines including interleukin-1 (IL1) (Dinarello, C. A., *Rev. Infec. Dis.* 6:51–94 (1984)), interleukin-6 (IL6), and colony stimulating factor (CSF) (Apte, R. N. et al., *J. Cell. Physiol.* 89:313 (1976)). Some of these cytokines further stimulate T lymphocytes to produce additional cytokines, for example, interleukin-2 (IL2) (Robb, R. J., *Immunol. Today* 5:203–209 (1984)). The monocyte-derived cytokines (or "monokines") are thought to be important mediators of the metabolic and neurohornmonal responses to endotoxic (Michie, H. R. et al., *N. Eng. J. Med.* 318:1481–1486 (1988)), and that seen in cancer (see below) and other catabolic states (Norton, J. A. et al., *Nutrition* 5:131–135 (1989)). Interestingly, some changes induced by low-dose TNF closely resemble changes provoked by high dose IL2 (Remick, D. G. et al., *Lab. Invest.* 56:583–590 (1987)).

In Vivo Effects of Endotoxin, TNF, and IL2

In a study of human volunteers, Revhaug, A. et al. (*Arch. Surg.* 123:162–170 (1988)) showed that endotoxin administration produced acute illness with flu-like symptoms including fever, tachycardia, increased metabolic rate and stress hormone release. Since the cyclooxygenase inhibitor, ibuprofen, markedly attenuated these changes, the cyclooxygenase pathway was implicated as playing a role in critical illness. Michie, H. R. et al. (Surgery 104:280–286 (1988)) treated cancer patients having normal kidney and liver function with escalating doses of TNF (4–636 $\mu g/m^2/24$ hr). Doses greater than 545 $\mu g$ $/m^2/24$ hr caused alterations similar to those induced by injection of endotoxin (4 ng/kg) into healthy humans. The authors concluded that TNF is the principal host mediator of septic and endotoxemic responses.

Intravenous treatment of cancer patients with 30,000 U/kg of recombinant IL2 (rIL2) provoked similar endotoxin-like effects, such as fever, tachycardia, flu-like symptoms, and stress hormone production (Michie, H. R. et al., *Ann. Surg.* 208:493–503 (1988)). Unlike endotoxin responses, these effects peaked later, and resulted in increased circulating concentrations of interfon-$\gamma$. Ibuprofen treatment attenuated the fever and stress hormone responses to IL2.

More recently, Michie, H. R. et al. (*Ann. Surg.* 209:19–24 (1989)) disclosed that 5 days of chronic intravenous TNF infusion into humans or rats was associated with anorexia, fluid retention, acute phase responses, and negative nitrogen balance (i.e., classic catabolic effects). It was concluded from this study that TNF may be responsible for many of the changes noted during critical illness. Further toxic effects in dogs following treatment with human recombinant TNF (rTNF) were demonstrated by Evans, D. A. et al. (*Ann. Surg.* 209:312-321 (1989)), who found that acute treatment over 6 hours with 57,000 U/kg caused a drop in blood pressure, a rise in heart rate, increase in urine volume, fever, tachycardia and hypermetabolism, increased stress hormones, leukopenia, and hypoglycemia. Most of these changes were abolished by ibuprofen treatment. It was concluded that sublethal doses of TNF caused acute responses similar to endotoxemia/septicemia, and that cyclooxygenase inhibitors represent a potentially important therapeutic for such states. Administration of rTNF to cancer patients also led to a rise in C-reactive protein (CRP) and a fall in serum zinc, a large increase in forearm efflux of total amino acids, and amino acid uptake by other tissues (Warren, R. S. et al., *Arch. Surg.* 122:1396-1400 (1987)). This is considered further circumstantial evidence for a role of TNF in cancer cachexia. Finally, Fraker, D. L. et al. (*Am. J. Physiol.* 256:E725-E731 (1989)) found that treatment with TNF at 100 $\mu$g/kg twice daily for 5 days induced cachexia in rats. Concurrent treatment with insulin (20 U/kg, twice daily) reversed changes in food intake, nitrogen balance and weight loss, a finding reminiscent of other forms of catabolic dysfunction.

TNF and Endotoxin in Cancer and Infectious Disease

The presence of high levels of endotoxins in cancer patients (Harris, R. I. et al., *J. Clin. Path.* 37:467-470 (1984)), particularly in patients with tumor types known to be associated with an increased incidence of cachexia (Humberstone, D. A. et al., *Cancer* 62:1619-1624 (1988)), has been noted. The presence of high endotoxin levels is probably not a direct result of the tumor per se, but rather reflects the general debility of the patients. It was recently postulated that increased translocation from the gut of endogenous bacteria and endotoxins in critical illness is dependent on the presence of malnutrition and that impaired cell-mediated immunity may be an aggravating factor (Wilmore, D. W. et al., *Surgery* 104:917-923 (1988)). As cachectic cancer patients are malnourished and often exhibit suppression of cell-mediated immunity, translocation of endogenous organisms may account for higher levels of endotoxins.

Aderka, D. et al., *Lancet* i: 1190-1192 (1985) found enhanced "spontaneous" TNF release in vitro from cancer patients' peripheral blood mononuclear cells. TNF production in response to macrophage-activating agents was reduced in patients with advanced metastatic disease but not in cancer patients with only localized disease. These observations supported the notion that TNF production is ongoing in cancer patients, either due to sustained stimulation of monocytes/macrophages by tumor cells or to direct TNF production by tumor cells. However, this study did not examine TNF levels in vivo nor show any relationship between TNF and actual cachexia.

TNF was detected in the serum of 50% of 226 cancer patients with active disease, compared to 3% of healthy sera and 18% of sera from disease-free cancer patients (Balkwill, F. et al., *Lancet* ii: 1229-1232 (1987)). The inducing stimulus and clinical significance of TNF production in cancer were not understood, although some human tumors, such as ovarian cancer, may actually produce TNF. The authors question the value of TNF therapy as an anti-cancer treatment in light of their observations.

TNF levels were also elevated in a variety of bacterial and viral illnesses. Lahdevirta, J. et al., *Amer. J. Med.* 85:289-291 (1988), disclosed elevated levels of TNF in serum of 9/9 AIDS and 5/9 AIDS-Related Complex patients, compared to controls or asymptomatic HIV-infected subjects, which may play a role in the cachexia seen in AIDS. Waage, A. et al., (*Lancet* i:355-357 (1987)) observed TNF in the serum of patients with meningococcal meningitis, septicemia, or both, which was positively correlated with mortality. In a rat burn/infection model, levels of hepatic TNF mRNA increased 100% in rats subjected to burn+infection (BI) compared to controls (C) or burn-only (B) rats (Marano, M. A. et al., *Arch. Surg.* 123:1383-1388 (1988)). Serum TNF was detected in 5/25 B rats (mean 1.3±0.2 $\mu$g/L) and 9/50 BI rats (mean 6.1±3.5 $\mu$g/L). Compared to the other groups, BI rats showed loss of muscle mass and carcass protein. Michie, H. R. et al., (*Br. J. Surg.* 76:670-671 (1989), reviewed evidence that TNF is the principal mediator associated with the changes of severe sepsis.

IL2 Deficiency and IL2 Therapy

IL2 is a lymphokine produced predominantly by T lymphocytes (Pfizenmaier, K. et al., *Eur. J. Immunol.* 14:33-39 (1984)) and has been considered a central regulator factor of the immune response (reviewed in: Robb, R. J., *Immuno. Today* 5:203-209 (1984)). IL2 actions include the stimulation of T cells to proliferate and become cytotoxic, the enhancement of B cell growth factor production, the induction of IL2 receptors and the enhancement of gamma interferon production (Robb, R. J., supra). In vitro studies of peripheral blood cells from patients suffering from catabolic diseases such as burns (Wood, J. J. et al., *Anals Surg.* 200:311-319 (1984), major trauma (Rodrick, M. L. et al., *J. Clin. Immunol.* 6:310-318 (1986)), and cancer (Monson, J. R. T. et al., *Br. J. Surg.* 73:483-486 (1986)), revealed a diminished capacity to produce IL2 in response to lectins. It was not clear whether this depression of IL2 production contributed to, or was simply the result of, the metabolic and nutritional abnormalities associated with these catabolic conditions.

The therapeutic use of IL2, both natural and recombinant (rIL2), to reconstitute immune deficiencies and treat a broad range of cancers, genital herpes, and other viral diseases, alone or in adjunctive therapy, has been suggested (Fiers, W. C. et al., European Patent Publication 0118977 (Sept 19, 1984); Mertelsmann, R. et al., European Patent Publication 0092163 (Oct. 26, 1983); Rosenberg, S. A. et al., *J. Exp. Med.* 161:1169-1188 (1985)).

Gough et al. (*Surgery* 104:292-300 (1988)) studied burnt mice which are highly susceptible to bacterial sepsis. Mitogen-stimulated IL2 production by their spleen cells was impaired. Addition of exogenous rIL2 at 100 U/ml in vitro restored mitogen responses of spleen T cells to normal after thermal injury. The in vitro administration (i.p) of rIL2 at doses of 16,000 U/day for 6 days after thermal injury improved splenic T cell responses in vitro and significantly enhanced survival following infection without causing generalized toxicity. A higher dose of IL2, 60,000 U/day, was in itself immunosuppressive, whereas protective activity was additionally observed with doses of 200 or 256,000 U/day. The authors concluded that IL2 at some doses, including low doses, may have therapeutic potential in the improvement of host defense against infection after thermal injury.

SUMMARY OF THE INVENTION

Recognizing the need in the art for therapeutic approaches for treatments for cachexia which is associated with cancer, infectious diseases, and other catabolic states, the inventor has developed the following invention. It is based on his recognition that patients suffering from the above mentioned diseases are typically immunosuppressed and therefore have inadequate IL2 production or activity. TNF, an important mediator in the induction of the cachectic state, is produced in an exaggerated manner by cells obtained from these patients, whereas IL2 serves as a down-regulatory signal for TNF production.

The invention, therefore, is directed to a method of treating cachexia in an animal comprising administration of interleukin 2 to the animal in an amount effective to prevent, ameliorate, or cure the cachexia or diminish the effects of excessive monokine production. In one embodiment, the cachexia is associated with cancer. In other embodiments, the cachexia is associated with infectious diseases, including bacterial infection and sepsis, viral infection, such as with human immunodeficiency virus-1, and parasitic diseases. The invention is also directed to treating cachexia associated with catabolic states resulting from surgery, sepsis, burn injuries, calorie deprivation, chemotherapy, radiation therapy, uncontrolled diabetes, and complications of endotoxin stimulation such as renal failure, adult respiratory distress syndrome, and the like, which have been linked to endotoxemia or TNF.

IL2 therapy according to the present invention, given in much lower doses than commonly employed in IL2 anti-tumor therapy protocols, represents a novel use of lymphokine therapy to achieve a distinct goal in the treatment of particularly difficult problems that accompany cancer and other diseases.

BRIEF DESCRIPTION OF THE DRAWINGS

FIG. 4A and 4B. Inhibition of TNF production by endotoxin and IL2. The upper panel shows TNF production by $5\times10^4$ adherent cells in response to increasing concentrations of IL2 (0 to 50 u/ml) in the presence of various concentrations of endotoxin (LPS). The lower panel shows TNF production by adherent cells in response to increasing concentrations of LPS in the presence of 10 u/ml IL2 and in the absence of IL2. TNF production was significantly lower in IL2-containing cultures ($p<0.002$, paired t-test).

FIG. 5A and 5B. Effect of polymyxin on TNF production in response to IL2 and endotoxin. The graphs depict TNF production by adherent cells in response to increasing concentrations of LPS (upper panel) or IL2 (lower panel) in the presence of polymyxin (500 u/ml).

FIGS. 13A, 13B and 13C are regular dose response curves. FIGS. 13A', 13B' and 13C' are dose log response curves.

DESCRIPTION OF THE PREFERRED EMBODIMENTS

Figure 1A:
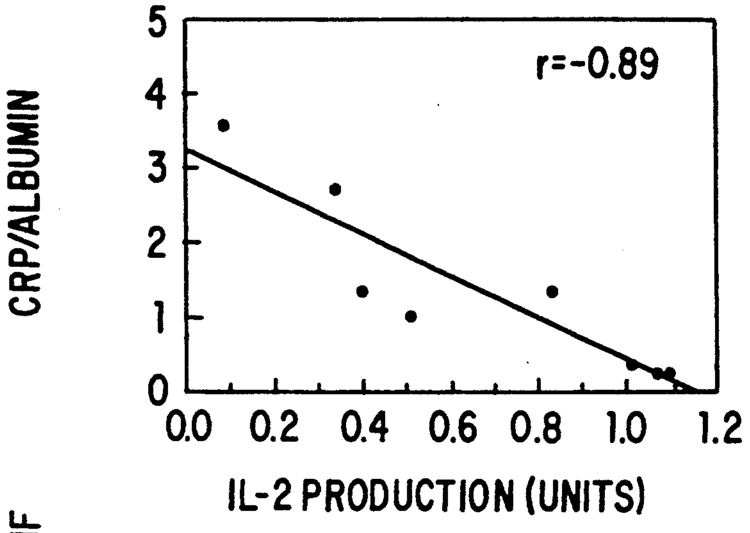
FIG. 1A–1C Graphical depiction of the relationship between IL2 production and (i) the acute phase responses, expressed as the CRP/Serum Albumin ratio (panel A); (ii) endotoxin stimulated TNF production, expressed as the ratio of stimulated/unstimulated TNF (Panel B); and (iii) suppression of the PHA response (Panel C). The correlation coefficients were determined to be $r=-0.89$ ($p<0.005$) for panel A; $r=-0.89$ ($p<0.005$) for panel B; and $r=-0.92$ ($p<0.001$) for panel C.

This invention is directed to a method of treated cachexia in an animal, wherein the cachexia is substantially associated with cancer, infectious diseases, and other catabolic states.

The term "treating" is intended to include the prevention, amelioration, or cure of a symptom or set of symptoms constituting a disease state.

The term "substantially associated with" a disease or state, as applied to cachexia or other symptoms for which the method of the invention is effective, means that the cachexia or other symptoms are known to be a pathological manifestation of, and are related to the pathophysiology of the disease or state.

The preferred animal subject of the present invention is a mammal. By the term "mammal" is meant an individual belonging to the class Mammalia. The invention is particularly useful in the treatment of human subjects.

The IL2 of this invention is either natural or recombinant IL2. Either glycosylated or unglycosylated IL2 is useful in this invention. The glycosylated form is preferred. As is understood by one of skill in the art, rIL2 or its analogues produced in bacteria are generally unglycosylated. Glycosylation can be achieved by chemical means or by production of the rIL2 or its analogues in eukaryotic cells such as yeast, insect, or mammalian cells, as is known in the art.

The term "functional analogues" as used herein, is intended to include fragments, variants, derivatives, substitution products, isomers, or homologues of IL2 which retain the characteristics of IL2. Preferred are those analogues such as, for example, IL2-ala (Amgen) or desalanyl, serine-125 human recombinant IL2 (Cetus), wherein one or more amino acid substitutions or deletions have been introduced to add stability in vivo, thereby increasing the biological half life or efficacy of the IL2.

A "fragment" of IL2 refers to any subset of the molecule, that is, a shorter peptide.

A "variant of IL2 refers to a molecule substantially similar to either the entire peptide or a fragment thereof. Variants may be conveniently prepared by direct chemical synthesis of the variant peptide, using methods well-known in the art. Alternatively, amino acid sequence variants of IL2 can be prepared by mutations in the DNA which encodes the synthesized peptide. Such variants include, for example, deletions from, insertions into or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants of IL2 ordinarily are prepared by site-directed mutagenesis of nucleotides in the DNA encoding the IL2 molecule or a fragment thereof, thereby producing DNA encoding the variant, and thereafter expressing the DNA in recombinant cell culture. The variants typically exhibit the same qualitative biological activity as the nonvariant IL2. The technique of site-specific mutagenesis is well known in the art, as exemplified by Adelman et al., DNA 2:183 (1983).

One group of variants are those in which at least one amino acid residue in the protein molecule, and preferably, only one, has been removed and a different residue inserted in its place. Such substitutions preferably are made in accordance with the following list when it is desired to modulate finely the characteristics of the IL2 molecule.

| Original Residue | Exemplary Substitutions | Original Residue | Exemplary Substitutions |
|---|---|---|---|
| Ala | gly; ser | Leu | ile; val |
| Arg | lys | Lys | arg; gln; glu |
| Asn | gln; his | Met | leu; tyr; ile |
| Asp | glu | Phe | met; leu; tyr |
| Cys | ser | Ser | thr |
| Gln | asn | Thr | ser |
| Glu | asp | Trp | tyr |
| Gly | ala; pro | Tyr | trp; phe |
| His | asn; gln | Val | ile; leu |
| Ile | leu; val | | |

Substantial changes in functional or immunological properties are made by selecting substitutions that are less conservative than those in the above list, that is, by selecting residues that differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. The substitutions in general are expected to be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

The activity of the IL2 variant is then screened in a suitable screening assay for the desired characteristic. For example, a change in the immunological character of the IL2 molecule, such as binding to a specific anti-IL2 antibody, is measured by a competitive type immunoassay. Changes in binding to IL2 receptors are measured by assays known in the art, such as competitive binding to IL2 receptor-bearing cells with radiolabeled IL2 or variants or fragments thereof.

An "analogue" of IL2 refers to a non-natural molecule substantially similar in biological activity to either the entire molecule or a fragment thereof.

A "chemical derivative" of IL2 contains additional chemical moieties not normally a part of IL2. The use of covalently modified derivatives of IL2 are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

Carboxyl side groups (aspartyl or glutamyl) are selectively modified by reaction with carbodiimides, such as 1-cyclohexyl-3-(2-morpholinyl-(4-ethyl)carbodiimide or 1-ethyl-3-(3-dimethyl aminopropyl)carbodiimide. Furthermore, aspartyl and glutamyl residues are converted to asparaginyl and glutaminyl residues by reaction with ammonium ions.

Glutaminyl and asparaginyl residues are deamidated to the corresponding glutamyl and aspartyl residues, for example, using mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(-diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(-succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: structure and Molecule Properties*, W. H. Freeman & Co., San Francisco, pp. 79–86 (1983), acetylation of the N-terminal amine, and, in some instances, amidation of the C-terminal carboxyl groups.

Such derivatized moieties may improve the solubility, absorption, and biological half life of IL2. The moieties may alternatively eliminate or attenuate any undesirable side effect of IL2. Moieties capable of mediating such effects are disclosed, for example, in *Remington's Pharmaceutical Sciences*, 16th ed., Mack Publishing Co., Easton, Pa. (1980).

As used herein, an "effective amount of IL2" is meant to refer to an amount of IL2 sufficient to suppress one or more of the following symptoms or states: cachexia, weight loss, or other symptoms substantially associated with excessive stimulation of monocytes with endotoxin including, but not limited to, anorexia, fever, malaise, fluid retention and edema, renal impairment, lung impairment, poor substrate utilization, hyperglycemia, stress hormone responses, and catabolism in a subject recipient.

The specific amount of IL2 required by each individual will be dependent upon the age, health, and weight of the recipient, kind of concurrent treatment, if any, frequency of treatment, and the nature of the effect desired. Generally, daily dosages of IL2 will be from about 1 ng to 10 μg per kg of body weight. Normally, from about 10 to 100 ng/kg/d, in one or more applications per day, and preferably about 15 to 60 ng/kg/day is effective to obtain the desired result. In an alternative approach, the IL2, particularly where formulated in a timed-release form, may be administered less frequently, i.e., every other day or every third day.

The IL2 treatment of the present invention may be administered by any means, routes, or pharmaceutical compositions that achieve their intended purpose. Amounts and regimens for the administration of IL2 can be determined readily by those with ordinary skill in the art. For example, administration may be by parenteral, subcutaneous, intravenous, intramuscular, intrapulmonary, intraperitoneal, intranasal, transdermal, rectal or buccal routes. Alternatively, or concurrently, administration may be by the oral route.

The pharmaceutical composition may be employed in dosage form such as tablets, capsules, powder packets, liquid solutions, suspensions, or elixirs for oral administration, or sterile liquid formulations such as solutions or suspensions for parenteral use. Where the composition is to be administered orally, the IL2 must be enterically coated in order to prevent gastric digestion or decomposition of the IL2. As is known in the art, enteric coatings do not permit release of a significant quantity of the drug until the dosage form passes into the small intestine. Enteric coating compositions are well known to the art and generally may be subdivided into three groups: 1) mixtures of fats and fatty acids; 2) shellac and shellac derivatives; and 3) cellulose acetate phthalates. This last group of compounds are preferred, but any of the enteric coatings known and in common use throughout the pharmaceutical industry are suitable for the practice of this invention.

Preparations for parenteral administration include sterile aqueous or non-aqueous solutions, suspensions, and emulsions. Carriers or occlusive dressings can be used to increase skin permeability and enhance cutaneous absorption.

The invention also relates to a medicament or pharmaceutical composition comprising IL2, the medicament being used for treating cachexia substantially associated with cancer, infectious diseases, and other catabolic states Having now generally described the invention, the same will be more readily understood through reference to the following example which is provided by way of illustration, and is not intended to be limiting of the present invention, unless specified.

EXAMPLE I

Interleukin 2 Regulation of TNF Production in Patients with Cancer Cachexia

A study of patients with advanced cancer indicates a correlation between suppressed T cell blastogenesis and enhancement by endotoxin of in vitro peripheral blood mononuclear cell (PBMC) TNF production (see Example II, below).

The purpose of the present study was to investigate the possibility that suppressed T cell function, with its concomitant reduction in IL2 production, is responsible for the enhanced TNF production associated with cancer. This study also relates such abnormal regulation of cytokine production to the acute-phase protein response, which is a marker of disturbed protein metabolism in the cancer patient.

A. MATERIALS AND METHODS

Patient Protocol

The study group consisted of 8 cancer patients, mean age (59.2±4.2 years), the majority of whom had lost weight and had evidence of both hypoalbuminemia and acute-phase protein synthesis (Table 1). All studies were performed on the same day and included measurement of PBMC PHA responses, IL2 production, and TNF production (with and without added endotoxin), as well as measurement of serum albumin, plasma C-reactive protein (CRP) and endotoxin levels. A group of 5 healthy laboratory staff were used as controls to determine control levels of PHA responsiveness, IL2 production, response, serum albumin, CRP, and endotoxin (Table 2).

Response of PBMC to PHA

Twenty mls of heparinized blood were overlain on an equal volume of Ficoll-Hypaque and centrifuged at 1200 rpm at 37° C. for 35 minutes. Interface cells were collected and washed three times in RPMI-1640 medium supplemented with L-glutamine (2 mM), 1% antibiotic antimycotic solution (10,000 units penicillin, 10,000 μg streptomycin and 25 μg fungizone) and HEPES buffer (10 mM). Unless otherwise stated, reagents for cell washing and culture were obtained from Grand Island Biological Company (GIBCO, Grand Island, N.Y.). Cells were counted, their concentration adjusted to $1\times10^6$ cells/ml in medium further supplemented with 5% fetal calf serum (FCS), and 100 μl were plated in microtiter plates. PHA (20 μl of a 125 μg/ml solution) (Difco Laboratories, Detroit, Mich.) was added to each well to achieve a final concentration of 10 μg/ml. Medium was added to attain equal well volumes. Each easy assay was performed in triplicate and "background" wells, with no added PHA, were included as controls. Following a 72-hour incubation at 37° in a 5% $CO_2$ atmosphere, 1 μCi per well of tritiated thymidine ($^3$H-Tdr) (Sigma Chemical Co., Dorset, UK) was added, the cultures incubated for 18 hours, and the plates frozen at −20° C. Cells were harvested using a PHD$^R$ automated cell harvester and the samples counted in a Liquid Scintillation Spectrometer to determine the uptake of $^3$HTdr. The mean uptake in counts per minute (cpm) for triplicate samples without PHA was subtracted from the mean of samples containing PHA to yield the PHA response. Percent suppression of the PHA response for each cancer patient, with respect to the mean of five healthy volunteers tested concurrently, was calculated using the formula:

$$\% \text{ Suppression} = (1 - (\text{mean patient cpm}/\text{mean control cpm})) \times 100$$

Generation of IL2 Supernatants

PBMC were isolated as above, cell concentrations adjusted to $1\times10^6$ cells/ml in complete medium, an 100 μl samples were added to six replicate wells. To stimulate IL2 production, 20 μl of PHA at 62.5 μg/ml was added to each of three wells per sample and final volumes were then adjusted to 250 μl with medium. Following a 24-hour incubation under conditions described above, cell-free supernatants were withdrawn and frozen at −20° C. for later assay.

IL2 Assay

Growth of the IL2 dependent cell line, CTLL-2, (Gillis, S. et al., *J. Immunol.* 120:2027-2032 (1979)) was used to determine relative IL2 concentration of supernatant samples. Samples of 50 μl were serially diluted in doubling dilutions from 1:2 to 1:128 with medium (containing 10% FCS and 2-merceptoethanol) in microtiter plates and incubated for 1 hour to assure a proper pH. CTLL-2 cells were washed free of their growth medium three times in medium without FCS, cell concentrations were adjusted to $5\times10^4$/ml and 50 μl of cells were added to each well. Plates were then incubated for 20 hours. Cell numbers were measured using a colorimetric assay (Mosmann, T. R., *J. Immunol. Methods* 65:55-62 (1983)). Color reactions were red on an ELISA plate reader following a 4 hour incubation with the chromogen, MTT, and overnight solubilization at room temperature. An IL2 standard containing 2.5 units/ml was incorporated in the assay for later determination of IL2 concentrations in units. Titration curves for each sample were analyzed with the computer program, "FLEXIFIT." The resulting parallel curves were compared to the standard IL2 curve to provide estimates of sample IL2 concentrations.

PBMC TNF Production

PBMC were isolated and plated in microtiter plates at $1\times10^6$ cells/well in 200 μl of media (as above). To generate TNF in the supernatants, 20 μl of *E. coli* 055-B5 endotoxin (Difco Laboratories, Detroit, Mich.), at a final concentration of 1.25 μg/ml, was added as the "low dose" endotoxin. A "high dose" of endotoxin, 6 μg/ml, was also used when cell numbers permitted. Samples were incubated as above for 24 hours at which time cell-free supernatants were collected and frozen at −20° C. for later assay.

TNF Bioassay

TNF activity was measured as cytotoxicity against the TNF-sensitive cell line, WEHI 164 (clone 13) (Espevik, T. et al., *J. Immunol. Methods* 95:99 (1986)) using a recombinant human TNF preparation (Sigma Chemical Co.) as a standard. The dose response curves were analyzed using the computer program, "ALLFIT" (De Lean, A. et al., *Am. J. Physiol.* 235:E97-E102 (1978)). The cytotoxicity curves generated by dilutions of the test supernatants were parallel to the standard TNF preparation. PBMC TNF production was then calculated in relation to the standard TNF preparation. The ratio of endotoxin-stimulated to unstimulated TNF production was calculated.

Assay of Endotoxin and CRP

Prior to collection the of blood, the proposed venipuncture site was first treated with iodine (2% in alcohol) and allowed to dry. Without touching the skin, 5 mls of blood were withdrawn and collected in sterile non-pyrogenic plastic syringes, transferred into pyrogen-free screw-capped heparinized glass tubes and mixed by gentle inversion.

The heparinized blood was centrifuged at 4° C. at 100×g for 10 minutes to obtain a platelet-rich plasma and transferred by pyrogen-free pipette to plastic tubes for storage at −20° C. A chromogenic limulus amebocyte lysate assay (Piotrowicz, B. I. et al., *Zbl. Bakt. Hyg. A.* 260:108-112 (1985)) was used to determine endotoxin concentrations. A fluorescence polarization assay kit (CTX) was used to measure CRP. The ratio of CRP/albumin was used as a combined inflammatory/-nutritional index to reflect the disturbed protein metabolism which relates to the prognosis of the patients (Ingelbleck, Y. et al., *Int. J. Vitamin Nutr. Res.* 55:91-101 (1985); Clark, R. G. et al., *Br. J. Clin. Practice* 63:2-7 (1988).

Statistical Analysis

A normal probability plot was used to assess data relating to albumin and PHA response, and means were compared using unpaired Student's t-test. A non-parametric test, the Mann-Whitney U test, was used to compare CRP, TNF and IL2. Correlation coefficients were determined using a "Minitab" statistics program (University of Pennsylvania, Philadelphia, Pa.). All values were expressed as mean±standard error. Probability (p) values below 0.05 were considered statistically significant.

B. RESULTS

PBMC IL2 Production and PHA Response

Mean IL2 production in cancer patients (0.67±0.14 units) (Table 3) was significantly less than in controls (2.6±0.7 units, $p<0.05$) (Table 2) and PHA responses were significantly suppressed in cancer patients (49.9±11.4%)($p<0.05$). These results indicate that T cell function in the cancer group was impaired. There was a significant inverse correlation between suppression of PHA response and IL2 production, $r=-0.92$, $p<0.005$ (FIG. 10), indicating an association between deficient IL2 production and poor T cell proliferative responses to the mitogen, PHA.

PBMC TNF Production

The production of TNF by unstimulated PBMC from cancer patients was variable (mean 3170 pg/ml, range 440-7513 pg/ml)(Table 1). Low concentrations of endotoxin (1.25 μg/ml) stimulated increased TNF production in only 2 patients (Table 3). TNF production (ratio of endotoxin stimulated/unstimulated) was inversely correlated with IL2 production ($r=0.89$, $p<0.002$, FIG. 1B) and correlated directly with suppression of the PHA response ($r=0.81$, $p<0.03$), indicating an association between impaired T cell function and enhanced TNF production.

The lack of stimulation of TNF production by 1.25 μg/ml endotoxin was overcome by increasing the concentration to 5 μg/ml (Table 3). The higher concentration of endotoxin stimulated TNF production in 4 of 5 patients (Table 3). The ratio of endotoxin stimulated to unstimulated TNf production in these 5 patients remained correlated with the suppressed PHA responsiveness ($r=0.92$, $p<0.05$) (Table 3).

Albumin and CRP

Mean serum albumin in cancer patients (33±2 g/l) (Table 1), was significantly less than in controls (46.2±0.9 g/l) (Table 2) and was outside the range of normal values generally observed in our laboratories (36-44 g/l).

CRP levels were significantly elevated in patients (51.2±15.5 mg/l) (Table 1) compared to controls (12±2.9 mg/l) (Table 2). The ratio of CRP/albumin, an index of persisting acute-phase protein synthesis, was positively correlated with TNF production (stimulated-/unstimulated ratio) ($r=0.88$, $p<0.03$, Table 3) and negatively correlated with IL2 production ($r=-0.89$, $p<0.0051$ FIG. 1).

Plasma Endotoxin

Four of the eight cancer patients and four of the five volunteers had detectable levels of endotoxin (<1 pg/ml) (Tables 1 and 2). No correlations were observed between endotoxin levels, parameters of T cell function, TNF production or acute-phase proteins.

C. DISCUSSION

This study demonstrated an association between reduced IL2 production and increased mononuclear cell TNF production following exposure to endotoxin, and related such enhanced TNF release to a marker of the disturbed protein metabolism of the cancer host, namely, the acute-phase protein response. Thus, the immune system, and in particular T cells, may have a major role in modulating "inflammatory" cytokine release in the cancer patient. The multiple influences on T cell function would make it a variable influence in the cancer host, and might thereby account for the observation that certain cancer patients become cachectic while others with a similar tumor burden do not.

TABLE 1

Patient Characteristics

| P | Age (years) | Diagnosis | Wt. Loss (%) | Alb. (g/l) | CRP (mg/l) | Endo (pg/ml) | TNF (U) (μg/ml); |
|---|---|---|---|---|---|---|---|
| A | 56 | Colon Ca(R)[1] | 20 | 31 | 8 | 0 | 0.99 |
| B | 57 | Colon Ca(R)[1] | 7 | 42 | 11 | 27 | 0.44 |

TABLE 1-continued

| P | Age (years) | Diagnosis | Wt. Loss (%) | Alb. (g/l) | CRP (mg/l) | Endo (pg/ml) | TNF (U) (μg/ml); |
|---|---|---|---|---|---|---|---|
| | | Patient Characteristics | | | | | |
| C | 51 | Colon Ca(R)[1] | 11 | 28 | 28 | 20 | 7.16 |
| D | 56 | Colon Ca(R)[1] | 10 | 28 | 101 | 2 | 5.28 |
| E | 52 | Colon Ca(R)[1] | 24 | 28 | 115 | 0 | 1.91 |
| F | 51 | Squam. Ca(NR)[1] | 0 | 42 | 15 | 0 | 7.51 |
| G | 76 | Colon Ca(R)[1] | 3 | 34 | 91 | 7 | 1.13 |
| H | 73 | Bladder Ca(R)[2] | 5 | 31 | 31 | 0 | 0.94 |
| Mean | 59 | | 10 | 33 | 51.2 | 7 | 3.17 |
| SEM | 3.5 | | 2.9 | 2.1 | 15.5 | 3.7 | 1.05 |

[1]Liver metastases
[2]Nodal metastases
Characteristics of patients (P) A-H, including: age in years; diagnosis; (Wt. loss) percent 6 month weight loss; (Alb) serum albumin; (CRP) C-reactive protein; (Endo) plasma endotoxin; and TNF(U) unstimulated tumor necrosis factor production. (R) primary tumor resected, (NR) primary tumor unresected.

TABLE 2

Healthy Volunteer Characteristics

| | Age (years) | Albumin (g/l) | CRP (mg/l) | Endo (pg/l) | IL2 (u/ml) | % Change in PHA Response |
|---|---|---|---|---|---|---|
| V1 | 24 | 48 | 13 | 1 | 1.82 | +30.6 |
| V2 | 31 | 46 | 4 | 1 | 0.50 | −19.7 |
| V3 | 31 | 48 | 12 | 6 | 5.90 | +1.0 |
| V4 | 41 | 43 | 22 | 0 | 2.51 | −3.5 |
| V5 | 26 | 46 | 9 | 7 | 2.55 | −8.6 |
| Mean | 33 | 46.2 | 12 | 3 | 2.60 | 0.0 |
| SEM | 3 | 0.9 | 2.9 | 1.4 | 0.70 | 11.4 |

The ages and results of volunteer V1-V5 are shown.
CRP: C-reactive protein; Endo: endotoxin; IL-2: PBMC IL2 production; % Change in PHA response: (+) enhancement; (−) suppression.

TABLE 3

Parameters of T-lymphocyte Function, Metabolic Response, and TNF Production in Cancer Patients

| Patient | PHA Resp. % supp. | IL2 units | CRP/alb ratio | TNF(L endo) Stim/unstim | TNF(H endo) Stim/unstim |
|---|---|---|---|---|---|
| A | 27 | 1.07 | 0.26 | 0.59 | 1.16 |
| B | 20 | 1.19 | 0.26 | 0.73 | 0.92 |
| C | 78 | 0.40 | 1.35 | 0.86 | 1.98 |
| D | 46 | 0.83 | 1.35 | 0.77 | 1.07 |
| E | 91 | 0.09 | 3.57 | 1.14 | ND |
| F | 6 | 1.01 | 0.36 | 0.73 | ND |
| G | 87 | 0.34 | 2.70 | 1.17 | ND |
| H | 44 | 0.51 | 1.00 | 1.00 | 1.24 |

The results of in vitro studies, on patients (A-H) PBMC assays are tabulated. PHA responses are shown as percent suppression compared to control; (IL2) interleukin-2 production; (CRP/alb) ratio of C-reactive protein to albumin; TNF (L Endo) TNF response, ratio of TNF production as a ratio of stimulated to unstimulated PBMC, at low endotoxin concentration (1.25 μg/ml; TNF (H endo): TNF response with high endotoxin concentration (5 μg/ml); (ND) not determined due to inadequate number of cells for testing the response.

Impaired T cell function is, however, common in patients who are old (Gillis, S. et al., *J. Clin. Inv.* 67:937-942 (1981)), malnourished (Schonland, M. M. et al., *Lancet* 2:435-436 (1972)), or recovering from major surgery (Rodrick, M. L. et al., *J. Clin. Immunol.* 6:310-318 (1986)). Therefore, the cumulative effects of the cancer state, old age, malnutrition and surgery may be responsible for the suppression of T cell function observed in our study.

Figure 1B:
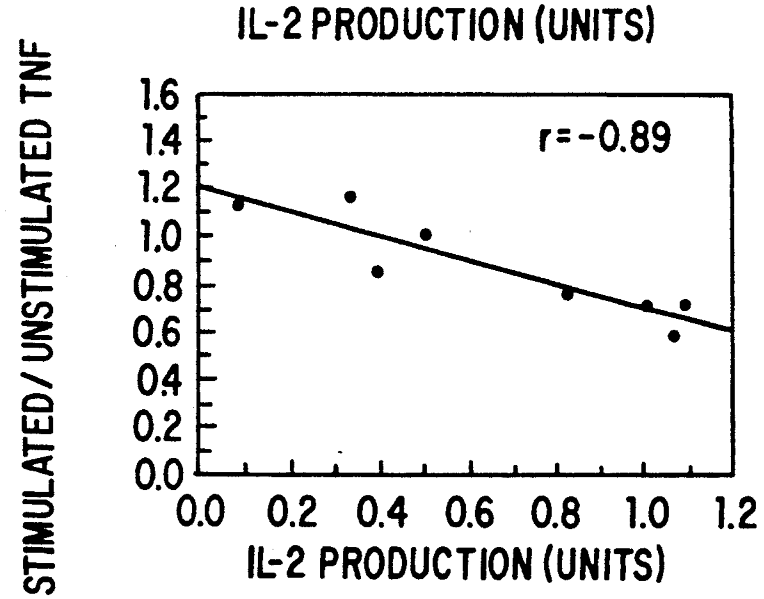
Figure 1C:
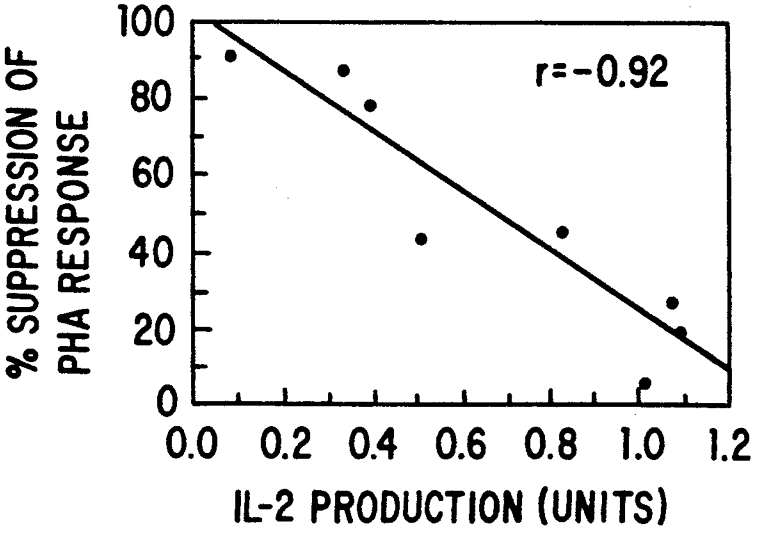

If the finding of impaired T cell function, manifested by an impaired response to PHA and decreased production of IL2, is important in the mechanism of cachexia, one would predict an association between IL2 and TNF production and parameters of altered metabolism. Such associations were demonstrated here. Suppression of the PHA response was correlated with increased TNF production in response to endotoxin and with increased CRP/albumin ratios. Moreover, decreased IL2 production was similarly correlated with increased TNF production and increased CRP/albumin ratios (FIG. 1A and 1B). Since PHA responses and IL2 production, both indices of T cell function, were significantly correlated in this group of patients (FIG. 1C), these data provide a link between immunosuppression, increased TNF synthesis and an acute-phase response in cancer patients.

The results suggest that, in the presence of adequate T cell function, exposure to low concentrations of endotoxin may in fact decrease the amounts of TNF being manufactured by the PBMC population. This may be of benefit to healthy humans, in whom transiently low concentrations of endotoxin (Table 2) would not result in the elaboration and secretion of TNF with a resulting acute-phase response. In addition, the results suggest that T cell function regulates sensitivity to endotoxin.

EXAMPLE II

Regulation of TNF Production in Healthy Humans and in Patients with Advanced Malignancy The following experiments were performed to study endotoxin activation of monocytes in the presence or absence of lymphocytes having varying functional capacity, or of IL2, a known promoter of T cell function. Production of TNF was used as an index of monocyte activation, and of the generalized capacity of the monocytes to secrete metabolically active cytokines. The experimental subjects, healthy young volunteers and elderly patients with debilitating metastatic colon cancer, were selected to provide for large variations in both immuno function and clinical status.

A. MATERIALS AND METHODS

Subjects

Subject characteristics are summarized (Table 4). Heparinized blood samples were obtained from six outpatients (mean age of 59.1±5.3 and mean six-month weight loss of 10.2±3.4%) with histological evidence of liver metastases secondary to colon cancer and five weight-stable healthy volunteers (mean age of 34.2±2.6). All blood samples were taken on the same morning and aliquoted immediately for both the isolation of PBMC, separation of adherent cells (monocyte fractions), and biochemical and hematological testing.

Responses of PBMC to PHA

These assays were performed as described in Example I.

Effect of Indomethacin and IL2 on PHA Response

In PBMC cultures prepared as in Example I, 1 μg/ml indomethacin or 50 units/ml IL2 (Sigma Chemical Co., St. Louis, Mo.; Catalogue No. T2367) were added. The responses to PHA, to PHA+INDO, and to PHA+IL2 were compared and the percent enhancement of the PHA responses with the addition of either IL2 or IND0 were calculated. Mean enhancement due to either indomethacin or IL2 (of three samples for each subject) was then calculated.

TNF Production by PBMC

PBMC were stimulated to produce TNF as described in Example I.

Adherent Cell (Monocyte) TNF Production

Following Ficoll-Hypaque density centrifugation of blood, mononuclear cells from each individual were divided into 6 aliquots and allowed to adhere to plastic petri dishes for 4 successive 30 minute periods. Nonadherent cells wre remove by gentle washing in the intervening periods. Adherent cells wre collected by a short incubation with 0.5% lidocaine, counted and subsequently cultured in medium, as in Example I, in the presence of 5 ng/ml of endotoxin. After 24 hours, supernatants were collected, frozen and later tested for TNF concentration.

TNF Bioassay

TNF was measured as described in Example I.

Statistics

Results are expressed as means and standard errors. Groups were compared using a "Minitab" statistics program. Normally distributed data were compared using unpaired and paired Student's t-tests as appropriate. Correlation coefficient were determined using linear regression analysis with the same statistics program. For non-parametric data (for example, the amount of TNf produced), Mann-Whitney U tests were used. Differences were considered significant for p values less than 0.05 on a two-tailed probability plot.

B. RESULTS

Monocyte Production of TNF

The addition of endotoxin (5 ng/ml) to adherent cells resulted in an increase in the production of TNF in 9 of the 11 subjects (Table 5). The TNF production was variable among patients (No endotoxin: 0.97-5.28 ng/$10^6$ cells; plus endotoxin: 0.48-12.82 ng/$10^6$ cells) and controls (No endotoxin: 0.28-3.72 ng/$10^6$ cells; plus endotoxin: 0.3-14.87 ng/$10^6$ cells). The large differences in age and clinical status of these subjects (Table 4) were not reflected in the baseline or stimulated TNF production by monocytes.

PBMC Production of TNF

The addition of endotoxin to unfractionated PBMC cultures resulted in a measurable increase in TNF production in 5 of 6 patients, but in only 1 of 5 controls (Table 5). The mean % enhancement of PBMC TNF production in response to endotoxin in patients compared to controls was 46±11%. Although absolute levels of both baseline (0.55±0.32 ng/ml) and endotoxin stimulated (0.74±0.43 ng/ml) TNF production in cancer patients were higher, the differences were not significantly different from control levels (Baseline: 0.24±0.06 ng/ml; Stimulated: 0.24±0.07 ng/ml), apparently due to the high variability in the patient group.

PHA Responses

The mean PHA response in patients (Table 7) (23.0±4.0 cpm ($\times 10^{-3}$)) was significantly reduced compared to controls (66.3±13.3)($p<0.04$). This finding indicates a marked impairment of T cell function in vitro in the elderly cancer patients.

A significant correlation was observed between enhanced TNF production in PBMC and the suppressed PHA response (Table 6). No correlation was found between enhanced TNF production in monocytes and the PHA response of PBMC.

Effect of Exogenous IL2 on PHA Responses In Vitro

The addition of IL2 (50 u/ml) significantly increased the PHA response in all patients and in 4 of 5 controls (Table 7), with an overall mean increase of 10.7±2.6%. Moreover, an inverse correlation was found between the "baseline" PHA response and the IL2-enhanced PHA response in all subjects ($r=0.783$, $n=11$, $p<0.005$), and in the cancer patients alone ($r=0.854$, $n=6$, $p<0.05$).

Effect of Exogenous IL2 on TNF Production by PBMC

Figure 2:
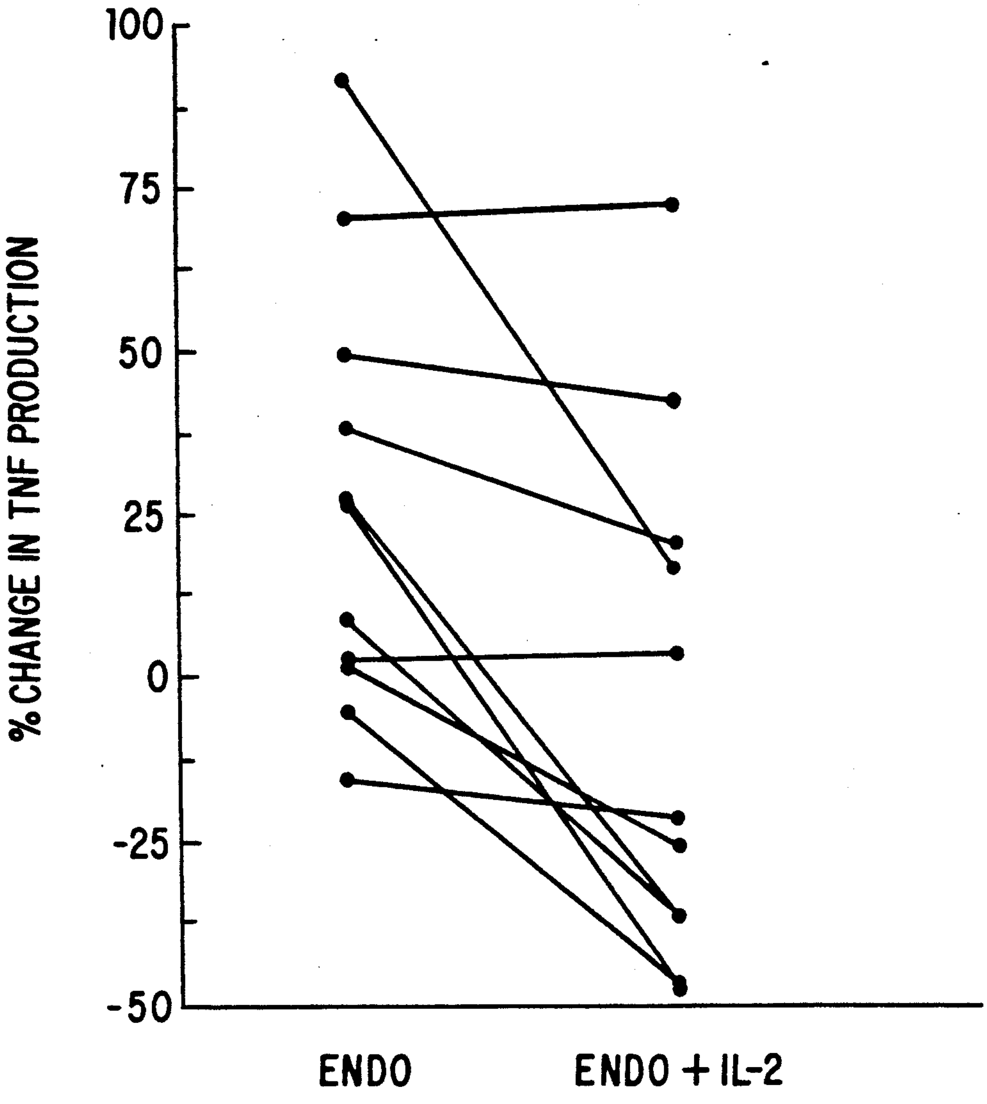
FIG. 2. Effect of IL2 on endotoxin-induced TNF production. The percentage change in TNF production following the addition of endotoxin (ENDO) (compared to baseline) was compared (paired t-test) for all subjects ($n=11$) in the presence and absence of exogenous IL2 (50 units/ml).

The presence of IL2 inhibited endotoxin-stimulated TNF production (over baseline) by PBMC for all subjects ($n=11$, $p<0.003$; FIG. 2). In contrast, IL2 alone, in the absence of endotoxin, stimulated TNF production ($n=11$, $p<0.001$; Table 6).

Thus, IL2 appeared to inhibit the TNF response to endotoxin of unfractionated PBMC, while at the same time being capable of stimulating TNF production on its own. Endotoxin-stimulated and direct IL2-stimulated TNF production were not correlated ($r=0.23$, $n=11$, $p<0.05$, Table 6).

Effect of Indomethacin (in Culture) on PHA Responses

The addition of indomethacin, which is known to inhibit monocyte production of prostaglandins which are inhibitory to lymphocyte proliferative responses, only marginally enhanced patient PHA responses (by 7.1±5.3%) (Table 7) and was weakly inhibitory in controls (−11.3±4.7%).

TABLE 4

| Parameter | Study Group Controls (n = 5) | Study Group Patients (n = 6) | p value |
|---|---|---|---|
| Age (years) | 34.2 ± 2.6 | 59.1 ± 5.3 | <0.001 |
| Weight loss [6 months] (%) | 00.0 ± 0.0 | 10.2 ± 3.4 | <0.03 |
| Albumin (g/l) | 46.2 ± 0.7 | 28.3 ± 3.3 | <0.001 |
| Total protein (g/l) | 68.1 ± 4.4 | 70.0 ± 2.2 | NS |
| C-reactive protein (g/l) | <10 all values | 85.8 ± 27.5 | <0.001 |
| Hemoglobin (g/dl) | 15.4 ± 0.5 | 11.1 ± 0.2 | <0.001 |
| White cell count (× 10/dl) | 6.0 ± 0.6 | 8.8 ± 1.7 | NS |
| Lymphocytes (%) | 51.2 ± 2.1 | 70.6 ± 4.3 | <0.001 |
| Monocytes (%) | 8.0 ± 2.0 | 9.0 ± 1.9 | NS |
| PHA response (cpm × $10^{-3}$) | 66.3 ± 13.5 | 23.0 ± 4.0 | <0.03 |
| PHA suppres- | 0 ± 19 | 65.3 ± 4.3 | <0.003 |

TABLE 4-continued

| Parameter | Study Group Controls (n = 5) | Patients (n = 6) | p value |
|---|---|---|---|
| sion (%) | | | |

Controls were 5 healthy individuals (designated G-K). Patients were 6 individuals with colon cancer and liver metastases (designated A-F). Each value is expressed mean ± SEM. NS denotes lack of statistical significance (Student's t-test).

TABLE 5

TNF Production in Monocyte and Peripheral Blood Mononuclear Cells

| | TNF[1] (Monocytes) LPS (ng/ml) | | | TNF[2] ( PBMC) LPS (μg/ml) | | |
|---|---|---|---|---|---|---|
| | 0 | 5 | % CHG | 0 | 1.25 | % CHG |
| Patient | | | | | | |
| A | 3.8 | 9.2 | 140 | 117 | 198 | 69 |
| B | 2.3 | 3.5 | 50 | 267 | 337 | 26 |
| C | 2.5 | 12.8 | 400 | 649 | 693 | 6 |
| D | 1.4 | 1.5 | 10 | 79 | 117 | 48 |
| E | 1.0 | 0.5 | −50 | 115 | 219 | 90 |
| F | 5.3 | 10.2 | 90 | 2100 | 2870 | 37 |
| Control | | | | | | |
| G | 1.0 | 0.6 | −42 | 320 | 400 | 25 |
| H | 0.3 | 0.3 | 7 | 139 | 116 | −17 |
| I | 1.3 | 14.9 | 770 | 107 | 74 | 1 |
| J | 3.7 | 8.7 | 130 | 208 | 194 | −7 |
| K | 1.0 | 5.7 | 460 | 401 | 400 | 0 |
| Comparison | NS[3] | NS | NS | NS | NS | $p < 0.001$ |

[1]TNF produced by monocytes is expressed in ng/$10^6$ cells.
[2]TNF produced by PBMC is expressed as pg/ml culture supernatant.
[3]NS - not significant ($p > 0.05$, Student's t test)
Patient (A-F) and control (G-K) TNF production in monocyte and PBMC cultures with the concentration of endotoxin (LPS) shown is provided along with the % change (% CHG) in baseline TNF production after exposure to endotoxin. % CHG preceded by (−) denotes a decrease in TNF production in the presence of LPS.

TABLE 6

Comparison of Endotoxin- and IL2-Induced PBMC TNF Production with Impairment of PHA Response

| | % INCREASE in TNF Production | | |
|---|---|---|---|
| | IL2 (50 u/ml) | Endotoxin (1.25 μg/ml) | % SUPPRESSION of PHA Response |
| Patient | | | |
| A | 53 | 69 | 84.8 |
| B | 386 | 26 | 56.1 |
| C | 69 | 7 | 64.5 |
| D | 64 | 48 | 62.5 |
| E | 13 | 90 | 78.3 |
| F | 10 | 37 | 45.8 |
| Control | | | |
| G | 209 | 25 | 29.6 |
| H | 79 | −17 | −43.4 |
| I | 50 | 1 | 26.7 |
| J | 77 | −7 | −54.0 |
| K | 141 | 0 | 40.5 |

(−) in column 2 denotes a decrease in TNF production in response to endotoxin.
(−) in column 3 denotes enhancement (rather than suppression) of the PHA response
Correlation of endotoxin-induced enhancement of TNF production
(a) with Suppression of PHA response: $r = 0.868$, $p < 0.001$
(b) with IL2 induced TNF production: $r = -0.23$, $p > 0.05$
Enhancement of TNF production, expressed as % INCREASE, in response to endotoxin (1.25 μg/ml) or IL2 (50 units/ml), and suppression of the PHA response compared to the mean for healthy controls is tabulated for patients A-F and controls G-K.

TABLE 7

Effect of In Vitro IL2 and Indomethacin on PHA Response

| | PHA Response | | Change in PHA Response | |
|---|---|---|---|---|
| | | | IL2 | Indomethacin |
| | cpm ($\times 10^{-3}$) | % Suppression | (50 units/ml) (%) | (1 μg/ml) (%) |
| Patient | | | | |
| A | 10.1 | (−84.8) | 23.0 | 1.0 |
| B | 29.2 | (−56.1) | 12.3 | 13.4 |
| C | 23.6 | (−64.5) | 18.4 | 10.2 |
| D | 24.9 | (−62.5) | 4.6 | 20.3 |
| E | 14.4 | (−78.3) | 21.2 | −15.0 |
| F | 35.9 | (−45.8) | 3.1 | 16.8 |
| Control | | | | |
| G | 46.7 | (−29.6) | 7.8 | −21.7 |
| H | 95.0 | (43.4) | 0.6 | −18.2 |
| I | 47.9 | (−26.7) | 11.7 | 2.7 |
| J | 102.0 | (54.0) | −1.9 | −16.3 |
| K | 39.9 | (−40.5) | 17.3 | −2.6 |

(−) denotes suppressed response
PHA responses, % suppression of the PHA response (compared to the control mean), and % enhancement of PHA response in the presence of IL2 and indomethacin are shown for 6 patients and 5 controls. Correlation in % suppression of the PHA (alone) with enhancement of the PHA response by IL2: $r = 0.783$, $p < 0.005$.

C. DISCUSSION

The large variations in TNF production (presumably by monocytes) occurring in the presence of lymphocytes in the unfractionated PBMC populations (Table 5) and the relationship of TNF production to impaired T lymphocyte function collectively suggest that the activity of T cells is responsible for the variation in TNF production. This conclusion is supported by the observation that a T cell product, IL2, inhibited TNF production in response to endotoxin (FIG. 2) while stimulating the PHA response (Table 7). These results point to an important role for T lymphocytes, not only in the modulation of the immune response, but specifically in the regulation of monocyte production of TNF, a monokine known to have a vital role in the metabolic effects of critical illness.

The activation of monocytes by endotoxin both in vivo and in vitro results in the increased TNF production (Kornbluth et al., supra; Dinarello, supra). TNF has profound effects on metabolism, minute quantities causing an acute-phase response when administered intravenously to humans. TNF has also been proposed as a mediator of cachexia associated with AIDS, cancer and sepsis, and may directly induce tissue destruction.

Although endotoxin is a potent stimulus for TNF secretion, the amount of TNF produced by patient cells is not always proportional to the endotoxin load. In fact, many humans have detectable levels of circulating endotoxin with no apparent clinical symptoms. For instance, the portal vein, which supplies the "resident monocytes" in the liver, Kupffer cells, is often contaminated with endotoxin (Jacob. A. I. et al., *Gastroenterol.* 72:1268-1270 (1977)), yet not all patients with high levels of endotoxin develop an acute-phase response. Similarly, the responses of individuals to sepsis, surgery and trauma, conditions often associated with acute-phase responses, vary considerably. It is important, therefore, to uncover a mechanism which controls the production of TNF in response to endotoxin.

Based on the above results, it is concluded that this apparently multicellular regulatory mechanism is not expressed by isolated monocytes in culture, since production of TNF by enriched monocytes in response to endotoxin was highly variable and did not follow a pattern (Table 5). Furthermore, no differences were found in TNF responses of controls compared to weight-losing cancer patients. In fact, the response of some controls was higher than that seen in patients.

In contrast, patterns could be discerned in the production of TNF in unfractionated PBMC cultures. First, the amount of TNF produced (baseline and stimulated) appeared higher in cancer patients (Table 5). Second, the endotoxin stimulation of TNF production was greater in patients and was correlated with depressed T cell function (Table 6). This finding leads to the suggestion that adequate T cell function and normal production of IL2 regulates TNF production in response to endotoxin. When IL2 production is adequate, TNF production in response to endotoxin is "normally" inhibited. When IL2 production falls below a certain level, the ability to down-regulate the TNF response to endotoxin becomes less effective.

This interpretation is supported by the finding that, in 9 of 11 subjects, IL2 inhibited endotoxin-stimulated TNF production (FIG. 2). The mechanism by which IL2 achieves this effect has been examined (see Example III, below).

Direct simulation of TNF production by IL2 as observed here has been noted by others, (Nedwin, G. E. et al. *J. Immunol.* 135:2492–2497 (1985)), and may be attributable, in part, to endotoxin contamination of IL2 produced by recombinant means. However, if this were the case, stimulation of TNF production by a given dose of IL2 (contaminated by a fixed quantity of endotoxin) should be correlated to the stimulation by endotoxin, which was not observed. Alternate inhibitory mechanisms include IL2-induced alteration of monocyte activity and competition between IL2 and endotoxin for monocyte receptor sites. IL2 acting on endotoxin receptors could explain why the side effects of high-dose IL2 therapy resemble endotoxin effects (Michie, H. R. et al., *Surgery* 104:280–286 (1988).

In summary, these results confirm the importance of T cell function in the regulation of responses to endotoxin and point to approaches for controlling endotoxin sensitivity via stimulation of T cell function, in particular, IL2. These findings suggest the possibility of therapeutic manipulations using IL2, cyclooxygenase inhibitors, or both, to treat immunosuppressed patients suffering the metabolic consequences of excessive TNF (and related monokine) production.

EXAMPLE III

A Shared Pathway for Endotoxin and IL2 in the Stimulation of Human Monocyte TNF Production A number of possible mechanisms might explain the similarity in the effects of IL2 and endotoxin on the one hand, and fact that IL2 appears to inhibit the effects of endotoxins (Example II), on the other. One such mechanism is competition between IL2 and endotoxin for common monocyte receptors. The following experiments were designated to investigate competition between IL2 and endotoxin in the activation of human monocyte TNF production.

A. MATERIALS AND METHODS

Isolation of Human Monocytes from PBMC

Blood was collected and PBMC were prepared as described in Example I. Monocytes were prepared as plastic adherent cells according to the method described in Example II.

Stimulation of TNF Production

Cells were plated at a concentration of $7.5\times10^4$ cells/ml in a volume of 0.5 ml in 12-well plates in a "checker-plate" pattern. In this way, increasing concentrations of either endotoxin (0, 5, 25, 50, 100, 500 and 100 ng/ml) or IL2 (0, 10, 20, 50, 100, 200, 400 u/ml) alone or a combination were added. In addition, polymyxin B (500 u/ml) was also added to each concentration of endotoxin and IL2. All additions of polymyxin, IL2 or endotoxin were made in volumes of 20 μl. The resulting combinations allowed the measurement of TNF production under the influence of the several concentrations of endotoxin, IL2, or both, with or without added polymyxin. Following incubation for 24 hours at 37° C. in an atmosphere of 5% $CO_2$, supernatants were withdrawn for later assay of TNF.

To rule out effects of endotoxin, IL2 or polymyxin in the TNF assay, these substances in various combinations and doses were also incubated without cells to serve as controls.

TNF Bioassay

TNF levels were measured as described in Example I.

Reagents

Sterile polymyxin B sulphate was aliquoted in concentrations of 5,000 units in 0.5 mls of PBS and stored frozen at −70° C. until use. Sterile recombinant IL2 (10,000 u/ml) was aliquoted in 20 μl volumes in PBS and stored frozen at −70° C. until use.

B. RESULTS

Effect of IL2 and Endotoxin on Monocyte TNF Production

Baseline TNF production (without added IL2 or endotoxin) was 1.97 ng/ml. Monocytes are highly sensitive to endotoxin, such that concentrations as low as 5 ng/ml stimulated TNF production to a level of 8.1 ng/ml (FIG. 3A).

Figure 3A:
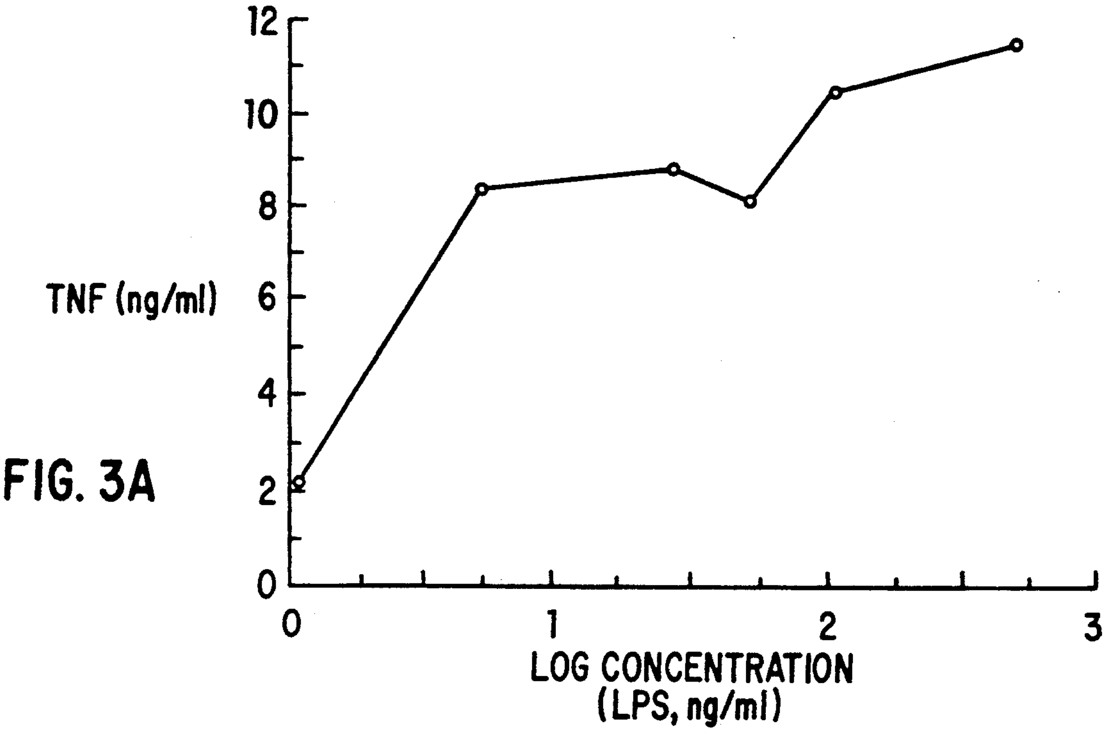
FIG. 3A and 3B. Effect of endotoxin and IL2 on monocyte TNF production. The amount of TNF produced by $5\times10^4$ adherent cells in response to increasing concentrations of *E. coli* endotoxin (LPS) (upper panel) or IL2 (lower panel) is plotted.

With increasing concentrations of endotoxin, a corresponding increase in TNF production was observed, to a maximum of 10.87 ng/ml TNF with 500 ng/ml endotoxin (FIG. 3A). Concentrations of endotoxin above 500 ng/ml appeared to be toxic, as less TNF was secreted (6.9 ng/ml in response to 1000 ng/ml of endotoxin).

Figure 3B:
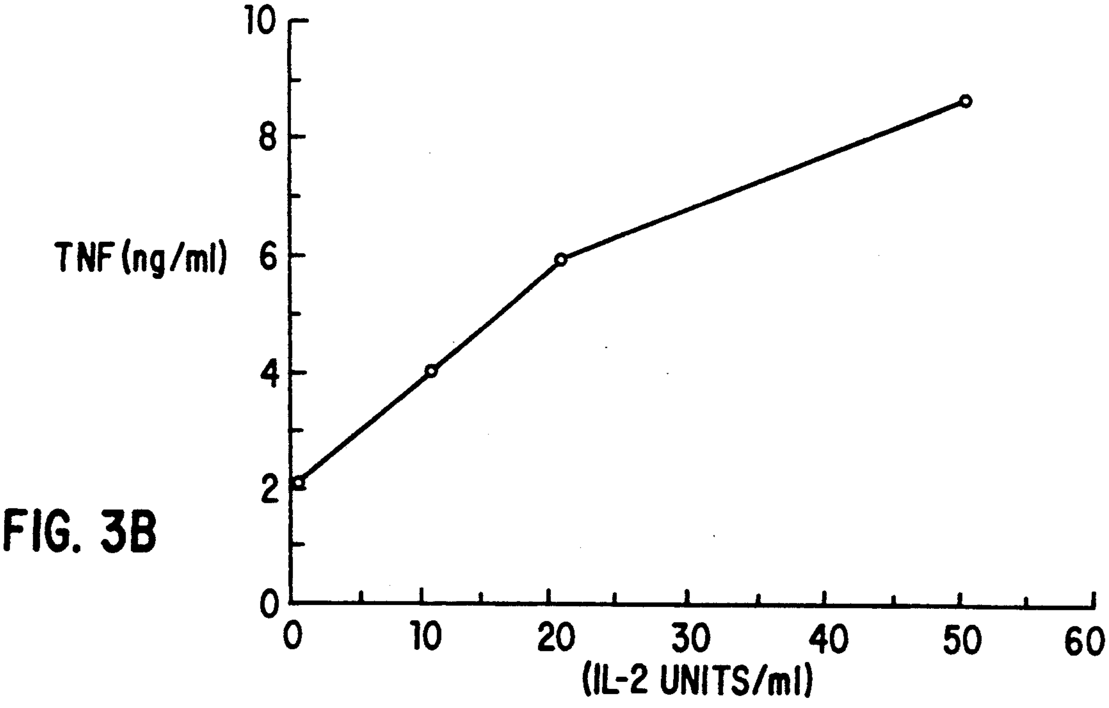

Similarly, increasing concentrations of IL2 also resulted in increased TNF production (FIG. 3B), to a maximum of 8.1 ng/ml with 50 units/ml of IL2. As with endotoxin, toxicity is believed to occur at higher IL2 concentrations, TNF production falling to 2.3 ng/ml at 100 units of IL2.

Therefore, both IL2 and endotoxin independently stimulated TNF production above baseline, in a dose-dependent manner up to what are believed to be toxic concentrations of the stimulants.

Effect of IL2 on Endotoxin-Induced TNF Production

The effects of various concentrations of endotoxin were tested in the presence of IL2, in order to determine whether IL2 could inhibit an expected endotoxin dose-dependent increase in TNF production. In the presence of a low concentration of IL2, 10 u/ml, increasing concentrations of endotoxin did not enhance TNF production (FIG. 4A). In fact, in the presence of 10 u/ml IL2, TNF production was inhibited about 50% relative to levels normally expected using the lowest concentration of endotoxin (e.g., 8 ng/ml of TNF for a concentration of 5 ng/ml of endotoxin). Therefore, low concentrations of IL2 inhibited endotoxin stimulation of TNF production.

The effects of higher concentrations of IL2 on the dose-response curves for endotoxin-stimulated TNF production were more complex. High concentrations of IL2 (without endotoxin) stimulated almost maximal TNF production; therefore, the further addition of endotoxin should have no further effect, particularly if both substances act via a common receptor.

However, although certain concentrations of endotoxin resulted in increased TNF production in the presence of higher concentrations of IL2, the expected increases associated with an increased in the concentration of endotoxin were not observed (Table 8).

TABLE 8

Effect of IL2 on TNF Production in Response to Increasing Concentrations of *E. coli* Endotoxin

| IL2 (u/ml) | Endotoxin (ng/ml) 0 | 5 | 25 | 50 | 100 | 500 |
|---|---|---|---|---|---|---|
| 0 | 1.97 | 8.06 | 8.41 | 7.62 | 9.93 | 10.86 |
| 10 | 3.07 | 3.74 | 4.58 | 3.70 | 3.89 | 3.36 |
| 20 | 5.59 | 6.38 | 10.73 | 7.09 | 7.39 | 10.26 |
| 50 | 8.10 | 7.87 | 13.68 | 6.72 | 7.78 | 5.89 |

Values represent TNF (ng/ml) produced by adherent cells ($5 \times 10^4$ cells/ml) in response to increasing concentrations of endotoxin in the presence (or absence) of IL2.

Effect of Endotoxin on IL2 Induced Monocyte TNF Production

The effect of various concentrations of endotoxin were also evaluated to determine whether they could inhibit the dose-dependent increase in TNF production induced by IL2. In the presence of 5, 50, 100 and 500 ng/ml of endotoxin, no increase in TNF production was induced by 10, 20 or 50 units of IL2, i.e., all values were below the level observed without IL2 (FIG. 4).

In the presence of 25 ng/ml of endotoxin, increases of 2.3 and 5.2 ng/ml of TNF, respectively, were produced in response to 20 and 50 u/ml of IL2 LEIGURE 4B. This amount was less than expected based on the effect of 20 and 50 u/ml of IL2 alone. Therefore, endotoxin appeared to inhibit the expected production of TNF in response to IL2.

Effect of polymyxin on IL2 and Endotin-Induced TNF

The effect of polymyxin on TNF production by monocytes in response to increasing concentrations of IL2 and endotoxin was tested. Polymyxin alone (500 u/ml) stimulated significant TNF production (6.23 ng/ml, FIG. 5A). However, no increase in TNF production was observed with the addition of 10, 20 or 50 u/ml IL2 (FIG. 5A and 5B).

Lower concentrations of endotoxin were also ineffective in stimulating TNF in the presence of polymyxin (FIG. 5A). Higher concentrations of endotoxin did evoke an increase in TNF production, although of lower magnitude than expected based on results of endotoxin alone (although maximum stimulation may have been reached).

C. DISCUSSION

Competitive inhibition at a receptor site requires that: 1) each of the two molecules must have similar actions on the receptor; (2) each must inhibit the action of the other; and 3) both must be blocked by a common agent, which may itself have a similar action on the receptor.

These experiments have shown that both IL2 and endotoxin each stimulated monocyte TNF production, and that each substance inhibited the action of the other. Furthermore, polymyxin, which could stimulate significant TNF production, inhibited the action of low doses of both IL2 and endotoxin. Therefore, the above criteria for competitive inhibition at a common receptor have been fulfilled.

Recombinant IL2 produced in *E. coli* may be contaminated by small quantities of endotoxin, which could account for the dose-dependent IL2 stimulation of TNF production and its inhibition by polymyxin. However, since recombinant IL2 also stimulates monocytes from endotoxin-unresponsive C3H/HeJ mice (Wahl, L. M. et al., *Infect. Immunol.* 23:8-13 (1979)), this argues for a role for IL2, rather than contaminating endotoxin, as a monocyte stimulant. Several reports have demonstrated IL2-induced activation of monocytes or their precursors see, for example, Baccarini, M. et al., *J. Immunol.* 142:118-125 (1989)).

It is interesting to note that polymyxin induced significant production of TNF (FIGS. 5A & 5B), suggesting that this agent itself had a potential to stimulate monocytes in an endotoxin-like fashion. Because of significant toxicity, especially renal toxicity, polymyxin is no longer used widely. Based on the above observation of polymyxin-induced stimulation of TNF, we suggest that the renal toxicity may be mediated, in part, by TNF, which has been known to produce acute renal pathology during endotoxemia (Hesse, D. G. et al., *Surgical Forum* XXI:680-682 (1988). This possibility is further supported by reports that polymyxin activates human monocytes to produce IL1 (Damais, C. et al., *J. Immunol. Meth.* 101:51-56 (1987)).

The known generalized toxicity of high doses of IL2 may also have a TNF-mediated component. In that case, if polymyxin and IL2 act at a similar monocyte (endotoxin) receptor, polymyxin may serve as an effective agent, in combination with IL2, in the treatment of advanced malignancy. By competitive inhibition at the monocyte receptor, polymyxin could prevent TNF-mediated side effects, allowing the use of increased concentrations of IL2. In fact, polymyxin reduces the lethality of high-dose IL2 in C3H/HeJ mice (see Example V and FIG. 7). This proposed action of polymyxin would be of considerable benefit to a patient with an IL2-responsive tumor whose therapy is often limited by IL2 toxicity (Rosenberg, S. A. et al., *N. Eng. J. Med.* 313:1485-1490 (1985).

Overlapping functional capacities of IL2 and endotoxin may explain many observations. First, it may be the basis for the similarity in in vivo toxicity of the two substances. Secondly, the fact that IL2 in certain concentrations may inhibit the actions of endotoxin on TNF production may provide an explanation for studies which suggested that an adequate amount of endogenous IL2 production may be protective in critical illness (Robb, R. J., *Immunology Today* 5:203-209 (1984)). This functional overlap would explain why the accelerated production of TNF in cancer patients in response to endotoxin was related to inadequate endogenous IL2 production (see Example I) and why this exaggerated production of TNF could then be blocked by the addition of exogenous IL2 (see Example II).

IL2 in high concentrations is known to cause increased expression of the IL2 receptor. Since several distinct IL2 receptors have been found on monocytes (Baccarini, M. et al., *J. Immunol.* 142:118-125 (1989); Herrmann, F. et al., *J. Immunol.* 142139-143 (1989)), the toxicity of high dose IL2 may be mediated by either such receptors (not responsive to endotoxin) or the proposed shared receptor, i.e., lipid A-associated protein receptor (see Example V). Only those subjects producing adequate amounts of IL2 would have sufficient numbers of the non-endotoxin related IL2 receptors to stimulate monocytes to antibacterial activity, which is highly desirable in the acute phase of bacterial infection.

In contrast, subjects immunosuppressed by disease or therapy, and failing to produce IL2 in sufficient quantities, would have deficient expression of IL2-induced (and specific) receptors potentially important for an IL2-monocyte amplification system. A deficiency in this monocyte amplification system in an immunosuppressed subject would lead to a thwarted monocyte secretion of agents necessary to deal with minor infection, and render the subject more susceptible to trivial infections.

In summary, the results of this experiment suggest that IL2 and endotoxin share a common monocyte activating ability which should be amenable to manipulation by IL2 or polymyxin in patients suffering from endotoxemia and exaggerated monocyte activation.

IL2 appeared more efficient at inhibiting endotoxin effects than endotoxin was at inhibiting IL2 effects. One explanation is that there is only one type of endotoxin receptor, which may be easily blocked by IL2, particularly if its affinity for IL2 is higher than its affinity for endotoxin. In contrast, several distinct types of IL2 receptors are known, and if only one is shared with endotoxin, an increase in the concentration of IL2 may engage or stimulate receptor sites which are not accessible to endotoxin.

The endotoxin receptor is composed of two basic parts, i.e., a lipid A-binding portion and a lipid A-associated protein (LAP)-binding portion. It is likely that IL2 would bind the LAP-binding part of the endotoxin receptor, leading to less monocyte activation than when endotoxin acts via the lipid A-binding portion. C3H/HeJ mouse monocytes do not express the Lipid A binding part of the endotoxin receptor which is fundamental to their state of hyporesponsiveness to endotoxin. We have shown competitive inhibition between endotoxin and IL2 on TNF production in these mice (see below), i.e. at the LAP binding site.

It is concluded that IL2 and endotoxin may both have access to the monocyte endotoxin receptor, giving rise to a functional overlap between IL2 and endotoxin in the process of monocyte activation. This overlap may explain the similarity in clinical "side" effects of IL2 and endotoxin and why patients with adequate endogenous IL2 production may be better able to cope with endotoxin and endotoxin-related critical illness. This analysis suggests an approach for inhibiting the systemic manifestations of critical illness which are mediated by excessive monocyte activation and monokine secretion.

EXAMPLE IV

An Association Between Impaired T Cell Function and Increased TNF Secretion in Patients with Cancer Cachexia Despite the evidence in support of the role of TNF in cachexia and in the metabolic response to endotoxins, increased plasma TNF levels are not always found (Waage et al., supra; Aderka et al., supra). Therefore, while it is recognized that TNF, or other cytokines, may be important in cancer and sepsis, measurement of plasma TNF levels has yielded little useful information for understanding why patients with similar tumor types and burdens vary in susceptibility to cachexia and in their metabolic response to both surgery and infection. Furthermore, the mechanism of regulation of TNF production in cancer patients is not known. In many of the conditions where TNF has been implicated as a mediator of catabolism or cachexia, impairment of T cell function is frequently evident, e.g. burns, cancer, AIDS, and endotoxemia.

The following study was performed to determine whether the host cell mediated immune response as reflected by in vitro T cell proliferative responses, modulates TNF production and is capable of regulating the metabolic response to tumor and endotoxins.

A. MATERIALS AND METHODS

Subjects

Patient data is summarized in Table 9. Ten patients with a mean age of 58.6±2.9, eight of whom were male, were studied. All patients had undergone resection of a colonic neoplasm at least two months prior to receiving the same regimen of hepatic intra-arterial chemotherapy for histologically proven livermetastases. Mean weight loss estimated over the previous 6 months by direct questioning of the group was 10.2%±2.3% of body weight.

Blood samples were drawn for hematological, biochemical and immunological tests one week after the previous dose of chemotherapy had been administered. Patients A-F were studied on the first day and patients G-J on the second. All blood samples were drawn over a 2 hour period on the morning of the study day. On each study day, blood from five healthy volunteers was taken to provide normal values for T cell function. Three of the volunteers were included on both days of the study.

PBMC Responses to PHA

Cell preparation and assay methods were described in Example I.

PBMC TNF Production

Methods were performed as described in Example I.

TNF Bioassay

The method was described in Example I.

Hematology and Biochemistry

Routine hematological tests were performed on patients and volunteers. Serum albumin was determined by routine methods. CRP levels were determined using a fluorescence polarization method (Abbott TDX); values less than 10 mg/ml were accepted as normal.

Statistics

Statistical evaluation of the data was performed as described in the previous Examples.

B. RESULTS

PHA Response

The mean PHA response for the five healthy normals on day 1 was 66.3±13.2 cpm ($\times 10^{-3}$) and on day 2 was 96.1±8.0 cpm ($\times 10^{-3}$). The PHA response for each cancer patient, and the % suppression compared to the mean of 5 controls (studied on the same day) are presented in Table 10.

The PHA response in the cancer patients was significantly suppressed (mean % suppression: 50.7±7.2%, $p<0.01$). Thus T cell function in the group of cancer patients was markedly impaired.

PBMC TNF Production

TNF responses, both background and to *E. coli* endotoxin, were highly variable. The amount of TNF produced and the ratio of stimulated/unstimulated are shown in Table 10. An increase in TNF production after exposure to endotoxin was not a constant finding.

T Cell Function and TNF Production

Figure 6:
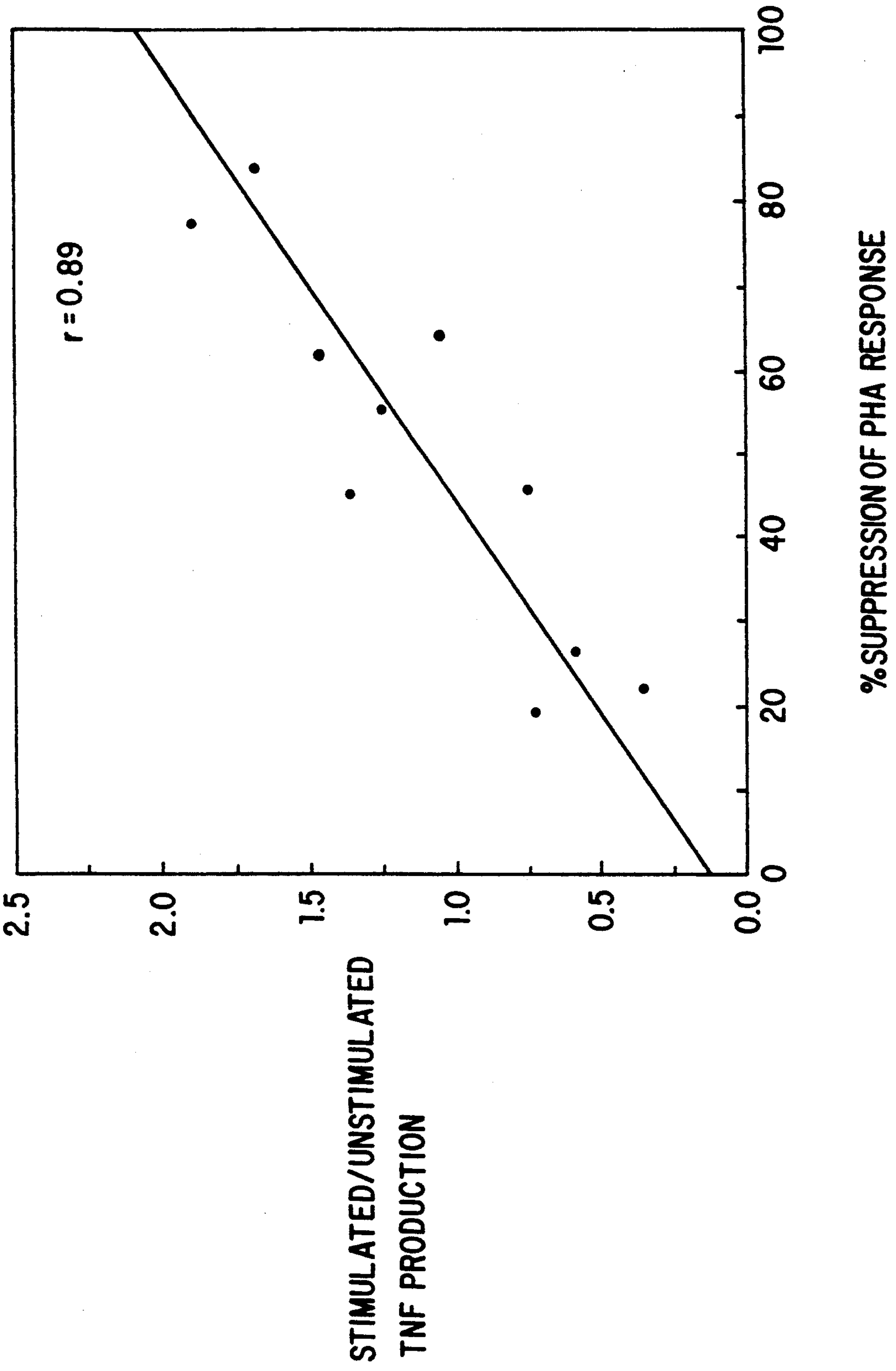
FIG. 6. The relationship between TNF production and PHA response in peripheral blood mononuclear cells (PBMC) of cancer patients. PHA responses are expressed as % suppression and TNF production is expressed as the stimulation index (ratio of endotoxin-stimulated to unstimulated TNF production).

There was a highly significant correlation, $r=0.89$, ($p=0.0005$) between suppression of the PHA response and TNF production expressed as the ratio of stimulated/unstimulated (FIG. 6).

The TNF ratio was >1 for cancer patients whose PHA response was suppressed by >45%. In cancer patients with near normal T cell function, endotoxin did not significantly stimulate increased TNF production, whereas such stimulation was observed in patients with defective T cell activity.

Hematology

Details of hematological tests are presented in Table 11. Although the monocyte population is the major source of TNF, no corelation was found between the monocyte counts or monocyte percentages and the ratio of stimulated/unstimulated TNF production. Similarly there was no correlation between total white blood cell number and TNF production.

Serum Albumin and CRP

Serum albumin and CRP levels are presented in Table 9. The mean Serum albumin concentration in the cancer patients was 29.9±2.3 g/l, 5 of the 10 patients concentrations of less than 30 g/l, and in 9, values were less than 40 g/l.

Elevated levels of CRP were found in 8 of 10 patients (group mean: 68.8±18.9 mg/ml). Therefore, the majority of the group showed evidence of persisting acute phase protein synthesis. In controls, albumin levels were always>40 g/l, and significant levels of CRP (10 mg/ml) were never detected.

TABLE 9

| Patient Characteristics, Serum Albumin and CRP | | | | | | | |
|---|---|---|---|---|---|---|---|
| Patient | Age | Sex | WT (kg) | HT (cm) | Weight Loss (%) | ALB (g/L) | CRP (mg/ml) |
| A | 68 | M | 079 | 176 | 03 | 36 | 10 |
| B | 50 | M | 065 | 185 | 06 | 34 | 19 |
| C | 54 | M | 063 | 168 | 25 | 18 | 130 |
| D | 73 | M | 072 | 163 | 06 | 36 | 107 |
| E | 67 | F | 032 | 150 | 15 | 21 | 69 |
| F | 43 | M | 077 | 170 | 06 | 25 | 180 |
| G | 56 | F | 052 | 170 | 20 | 31 | <10 |
| H | 57 | M | 067 | 175 | 07 | 42 | <10 |
| I | 62 | M | 065 | 185 | 04 | 28 | 44 |
| J | 56 | M | 059 | 173 | — | 28 | 104 |

The characteristics (age, sex, height, weight, percent weight loss) of patients A-J are tabulated in addition to serum albumin (ALB) and C-reactive protein (CRP).

TABLE 10

| PHA Response and TNF Production | | | | | |
|---|---|---|---|---|---|
| | PHA | % | TNF Response (pg/ml) | | |
| Patient | Resp | Supp | Unstim | Stim | (S/U) |
| A | 10.1 | 85 | 117 | 198 | 1.69 |
| B | 29.2 | 56 | 267 | 337 | 1.26 |
| C | 23.6 | 65 | 649 | 693 | 1.56 |
| D | 24.9 | 63 | 79 | 117 | 1.48 |
| E | 14.4 | 78 | 115 | 219 | 1.90 |
| F | 25.9 | 46 | 2100 | 2870 | 1.37 |
| G | 70.5 | 27 | 986 | 580 | 0.59 |
| H | 78.2 | 20 | 452 | 330 | 0.73 |
| I | 74.8 | 22 | 3480 | 1247 | 0.36 |
| J | 52.0 | 46 | 5301 | 4057 | 0.77 |

The PHA response of PBMC is shown in cpm $\times 10^{-3}$. The percent suppression (% Supp) is relative to the mean for healthy controls. PBMC production of TNF is shown (as pg/ml culture medium) unstimulated (U) or stimulated with endotoxin (S). The stimulation index (ratio of stimulated to unstimulated TNF production, S/U) for each patient was also calculated.

TABLE 11

| Hematology Results | | | | | | | |
|---|---|---|---|---|---|---|---|
| Patient | WBC ($\times 10^9$/L) | Poly (%) | Ly (%) | Mo (%) | Mo ($\times 10^9$/L) | Hb (g/dl) | Plt ($\times 10^9$/L) |
| A | 2.3 | 52.0 | 36.0 | 10.0 | 0.23 | 11.4 | 358 |
| B | 11.7 | 67.0 | 19.0 | 11.0 | 1.28 | 11.0 | 512 |
| C | 12.3 | 76.0 | 10.0 | 14.0 | 1.72 | 11.0 | 211 |
| D | 8.2 | 75.0 | 16.0 | 4.0 | 0.33 | 11.8 | 323 |
| E | 5.6 | 82.0 | 11.0 | 3.0 | 0.17 | 11.1 | 296 |
| F | 12.9 | 72.0 | 16.0 | 12.0 | 1.55 | 10.4 | 296 |
| G | 2.0 | 35.0 | 50.0 | 11.0 | 0.22 | 10.8 | 141 |
| H | 4.6 | 40.0 | 54.0 | 5.0 | 0.23 | 13.6 | 236 |
| I | 5.5 | 80.0 | 14.0 | 4.0 | 0.22 | 11.1 | 184 |
| J | 12.1 | 82.0 | 9.0 | 7.0 | 0.85 | 10.0 | 568 |

The hematology results for peripheral blood from patients A-J are tabulated and include white blood cell count (WBC), percent (%) polymorphonuclear leucocytes (Poly), lymphocytes (Ly), monocytes (Mo), total monocyte count (Mo $\times 10^9$/L), hemoglobin (Hb) and platelet count (Plt).

C. DISCUSSION

Patients whose PHA response was impaired showed considerable enhancement of TNF production in response to endotoxin (Table 10). This result may be due to a regulatory mechanism whereby cells present in the PBMC population limit, or in some cases suppress, monocyte TNF production and/or secretion. The correlation between suppressed T cell blastogenesis and TNF production suggests modulation of TNF by T cells or their products, such as IL2. Monocyte receptors for this lymphokine have been identified.

Many conditions associated with impaired T cell function, such as burns, AIDS, and endotoxemia, are frequently complicated by a prolonged catabolic response. Impaired cell mediated immunity is a poor prognostic sign for the surgical patient (Munster, A. M. et al., *Ann. Surg.* 194:345-352 (1981)). The association described here between depressed T cell responsiveness and a strong TNF response to endotoxin may underlie the prognostic significance of depressed cell mediated immunity.

By examining responses of unfractionated PBMC, as was done here, one provides an in vitro environment more closely resembling the in vivo situation, allowing detection of interactions between cells, while avoiding the difficulties associated with in vivo detection of TNF (which has a half-life of only 6 minutes).

The patient group consisted of patients with a similar tumor type and bulk undergoing identical treatment protocols. All patients had lost weight, and many had evidence of acute phase protein synthesis and or low levels of serum albumin (Table 9). However weight loss and general parameters of cachexia were high variable. Plasma endotoxin load, presumably a major stimulus to TNF production in vivo, was variable, leading to variable in vitro thresholds of monocyte activation and TNF production. Thus cancer patients with impaired T cell function may be at considerable risk of translocating endogenous gut organisms and endotoxins and, at the same time, may be excessively sensitive to the endotoxin stimulation of TNF.

The implications of these findings are widespread. First, the main source of TNF production in cancer patients may well be the peripheral blood, though TNF production may be occurring in the tumor or in other tissues. Second, if T cell function has a major bearing on the development of cachexia and on the response to endotoxins, then identification of the mechanisms involved might provide a therapeutic strategy for the treatment of cachexia in cancer patients and hypercatabolism in conditions associated with endotoxemia and impaired T cell function.

EXAMPLE V

In Vivo and in Vitro Interleukin 2 Induce Endotoxin-Like Effects in Endotoxin Hyporesponsive C3H/HeJ Mice Much of our understanding of the mechanism of action of endotoxins (lipopolysaccharide, LPS) comes from studies performed in an endotoxin-hyporesponsive mouse strain, C3H/HeJ. These animals lack the gene which confers sensitivity to the lipid A component of LPS due to the absence of the portion of the receptor which binds the lipid A portion of the LPS molecule. Thus when monocytes from these animals are stimulated with endotoxin preparations containing mostly lipid A, but little lipid A-associated protein (LAP), they do not respond (e.g. by secreting CSF, IL1, TNF or PGE2).

This mouse strain was used here to investigate whether the similarities in the effects of endotoxin and IL2 (both in vivo and in vitro) are due to biological similarities of the two molecules rather than to potential endotoxin contamination of IL2 produced by recombinant means.

A. MATERIALS AND METHODS

Animals

Male, endotoxin-hyporesponsive C3H/HeJ mice and endotoxin-sensitive A/J mice (Jackson Laboratories, Bar Harbor, Me.), 7 to 9 weeks old were used in all experiments. They were acclimatized for one week before use and had free access to standard mouse chow and water.

Reagents

Human recombinant IL2-ala having a specific activity of $7.5\times10^6$ units/mg (a gift from Dr. Bruce Altrock, Amgen Corp., Thousand Oaks, Calif.) was diluted with sterile 5% dextrose to appropriate concentrations for in vivo and in vitro use. Limulus amebocyte lysate testing of the IL2 dilutions indicated endotoxin levels below 1 ng. *E. coli* -55-B5 endotoxin (Boivin extracted, protein concentration of 2-9%, Difco Laboratories) was dissolved in sterile 0.9% sodium chloride in the appropriate concentration for in vivo and in vitro use. Polymyxin B sulphate (Sigma Chemical Company, St. Louis, Mo.) was dissolved in sterile 0.9% sodium chloride to be injected (500 units per animal) in the volume specified.

Isolation of C3H/HeJ Splenic Adherent Cells (SAC)

C3H/HeJ mice (n=20) were sacrificed by $CO_2$ asphyxiation and their spleens were removed, and teased apart. A pooled cell suspension was prepared (as described for blood cells in Example I) in medium supplemented with 2-mercaptoethanol ($5\times10^{-5}$M) and 10 mmol HEPES buffer (see Example I). Cells were washed twice in medium by centrifugation at 1500 rpm for 10 minutes and resuspended in a medium additionally supplemented with 20% Fetal Calf Serum (FCS). Cells were then allowed to adhere to plastic petri dishes ($1.8\times10^7$ cells/ml) at 37° C. in an atmosphere of $5CO_2$. After 1 hour, nonadherent cells were washed free, the procedure was repeated, and adherent cells were then lightly brushed off with soft rubber, were diluted in medium with 5% FCS and were counted.

Stimulation of Prostaglandin E2 (PGE2) Production by SAC

SAC were plated in flat-bottomed 96 well microtiter plates and LPS (0.01 to 1 mg/ml) or IL2 (25, 50, 100 or 200 u/ml) was added. As controls, an equal volume of either sterile saline (vehicle for LPS) or 5% dextrose (vehicle for IL2) was also added where appropriate. Following a 48 hour incubation at 37° C. in 5% $CO_2$, cell-free supernatants were collected and frozen at −70° C. for later analysis of PGE2 concentration.

Measurement of PGE2

Supernatant PGE2 concentrations (mean of duplicate samples) were analyzed using a radioimmunoassay kit (Seragen Research Products, Boston, Mass.; catalog #SG6001) and compared to a standard curve plotted for concentrations of PGE2 ranging from 27 to 27000 pg/ml.

In Vivo Assay of IL2, Endotoxin and Polymyxin

In vivo administration of agents was by intraperitoneal ip injection in 0.5 ml. Mortality of mice was assessed over the following 6 day period. Equal volumes of IL2 (in 5% dextrose), LPS (in normal saline), or polymyxin (in normal saline) were used in all experiments where the in vivo effects of one of these agents was compared to the effects of another. In addition, an equal number of injection stabs were used in all comparative experiments.

B. RESULTS

Sensitivity of C3H/HeJ Mice to Endotoxin

Groups of 10 mice were injected with doses of endotoxin of 0.25, 0.5, 1, 2, and 4 mg/mouse. Although the mice were relatively resistant to doses that would normally kill endotoxin-sensitive mice (0.5 mg did not kill any mice), doses of 2 mg of more killed all mice within 24 hours. Following injections of 1 mg, 4/10 mice died during the 6 day observation period.

Sensitivity of C3H/HeJ Mice and A/J Mice to IL2 In Vivo

Injection of 150,000 units of IL2 (thrice daily for 3 days) to 6 A/J mice did not result in a single mortality. Administration of the same dose to C3H/HeJ animals killed 5 of 6 mice after 4 days ($p<0.005$ for comparison of survival).

Effect of Polymyxin on IL2-Induced Mortality

The next experiment was designed to establish whether pretreatment with polymyxin reduced the mortality expected following injection of high doses of IL2 (210,000 units, thrice daily for 3 days).

Figure 7:
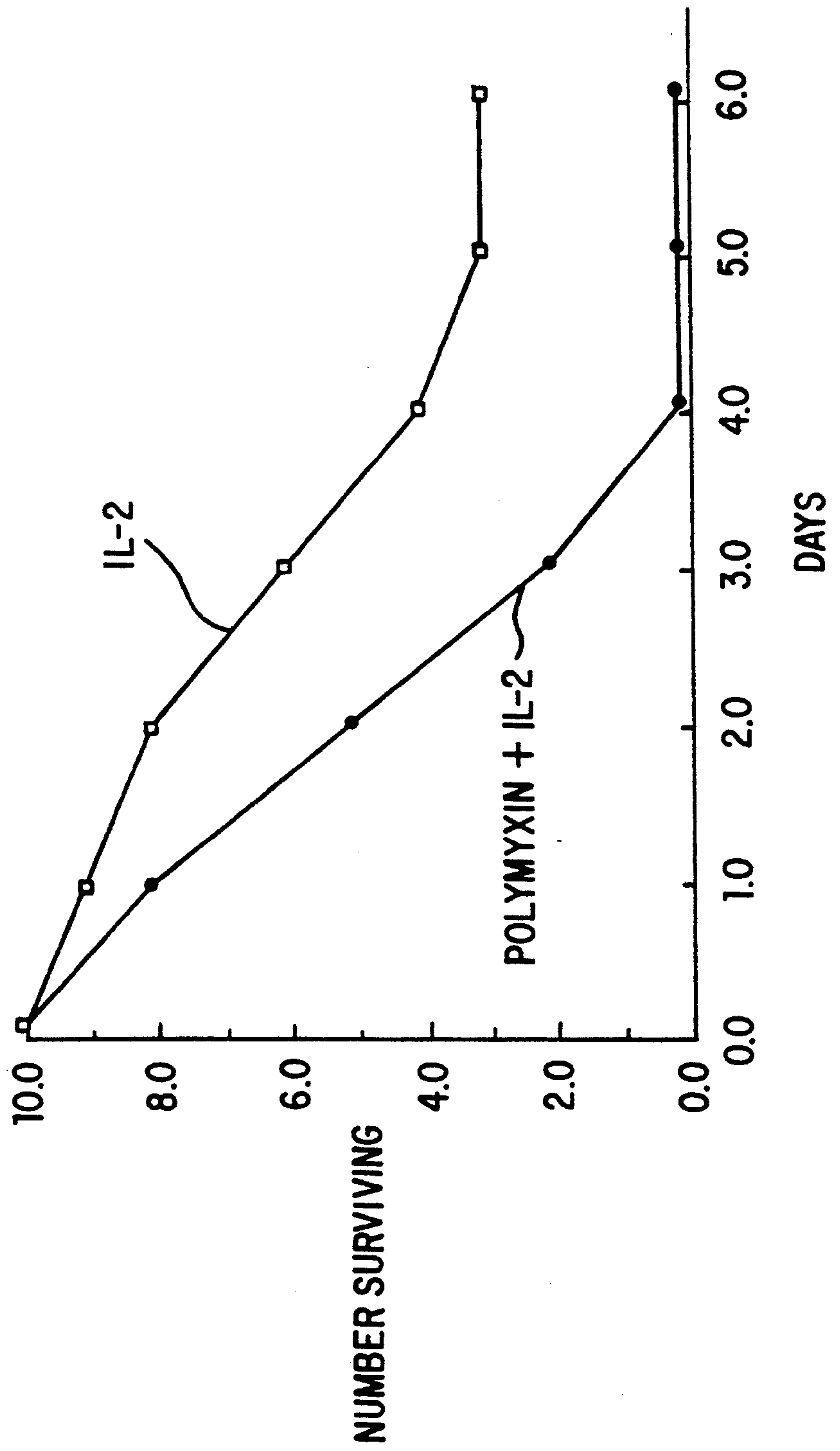
FIG. 7. Effect of polymyxin treatment on survival of endotoxinhyporesponsive C3H/HeJ mice following IL2 administration. The survival of mice following injection with either IL2 after prior saline injection ($n=10$) or IL2 after prior polymyxin injection ($n=10$) is presented.

Twenty C3H/HeJ mice received 210,000 units of IL2 and half got either 500 units of polymyxin or saline 90 minutes before the first daily injection of IL2. All animals received the same volume and number of daily injections. Survival was assessed for 6 days (FIG. 7). Mice receiving polymyxin had a significantly higher survival rate than the saline controls ($p<0.05$). Therefore polymyxin appeared to abrogate the lethality of IL2 in endotoxin-hyperresponsive C3H/HeJ mice.

Effect of Repeated Sublethal Doses of IL2 on Survival

C3H/HeJ mice were randomized to three groups of 8 mice. Group A received a single dose of 2,100,000 units of IL2 (in 0.3 mls) on day 1, followed by injections of 5% Dextrose (0.1 ml) thrice daily for 3 days. Group B received a single injection of IL2 (700,000 units in 0.1 ml) daily for 3 days in addition to twice daily injections of 5% dextrose for the same period. Group C received 3 injections per day of 233,000 units IL2 (in 0.1 ml) for 3 days.

Figure 8:
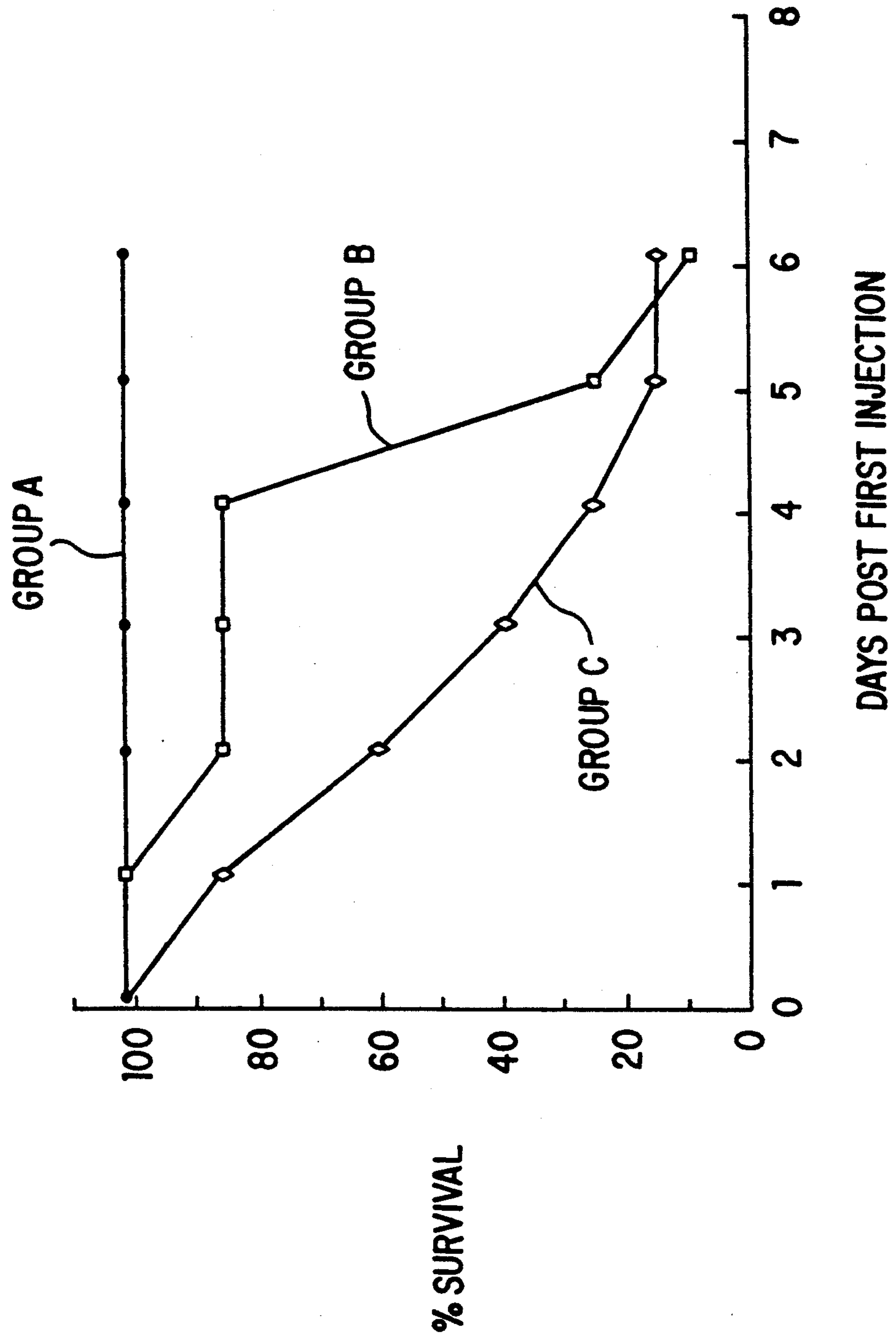
FIG. 8. Effects of repeated administration of sublethal doses of IL2 on survival of endotoxin-hyporesponsive C3H/HeJ mice. Three treatment protocols ($n=10$ per group) were compared in which each group of mice received the same total IL2 dose, the same number of injections and identical volumes of vehicle (5% dextrose) intraperitoneally over 3 days. Group A: $2.1\times10^6$ units (~276 μg) IL2 as a single injection on day 0 followed by 8 vehicle injections over 3 days. Group B: 3 daily injections of $7\times10^5$ units (·92 μg) IL2 interspersed with 6 vehicle injections. Group C: 9 injections of $2.33\times10^5$ units (~31 μg) IL2 over 3 days.

In this design, therefore, animals in each group received the same total dose of IL2, 2,100,000 units, the same volume of fluid, 0.9 ml, and the same number of ip injections (9) over the 3 day period. The results are shown in FIG. 8.

IL2-induced mortality increased when divided doses were used. Group A had a higher survival rate than group B ($p<0.005$), which in turn had a higher survival rate than group C ($p<0.005$).

This result suggests that multiple sublethal doses produced greater lethality than a single high dose, possibly due to a "sensitization" reaction to IL2.

In Vitro Production of PGE2 by C3H/HeJ SAC

Figure 9:
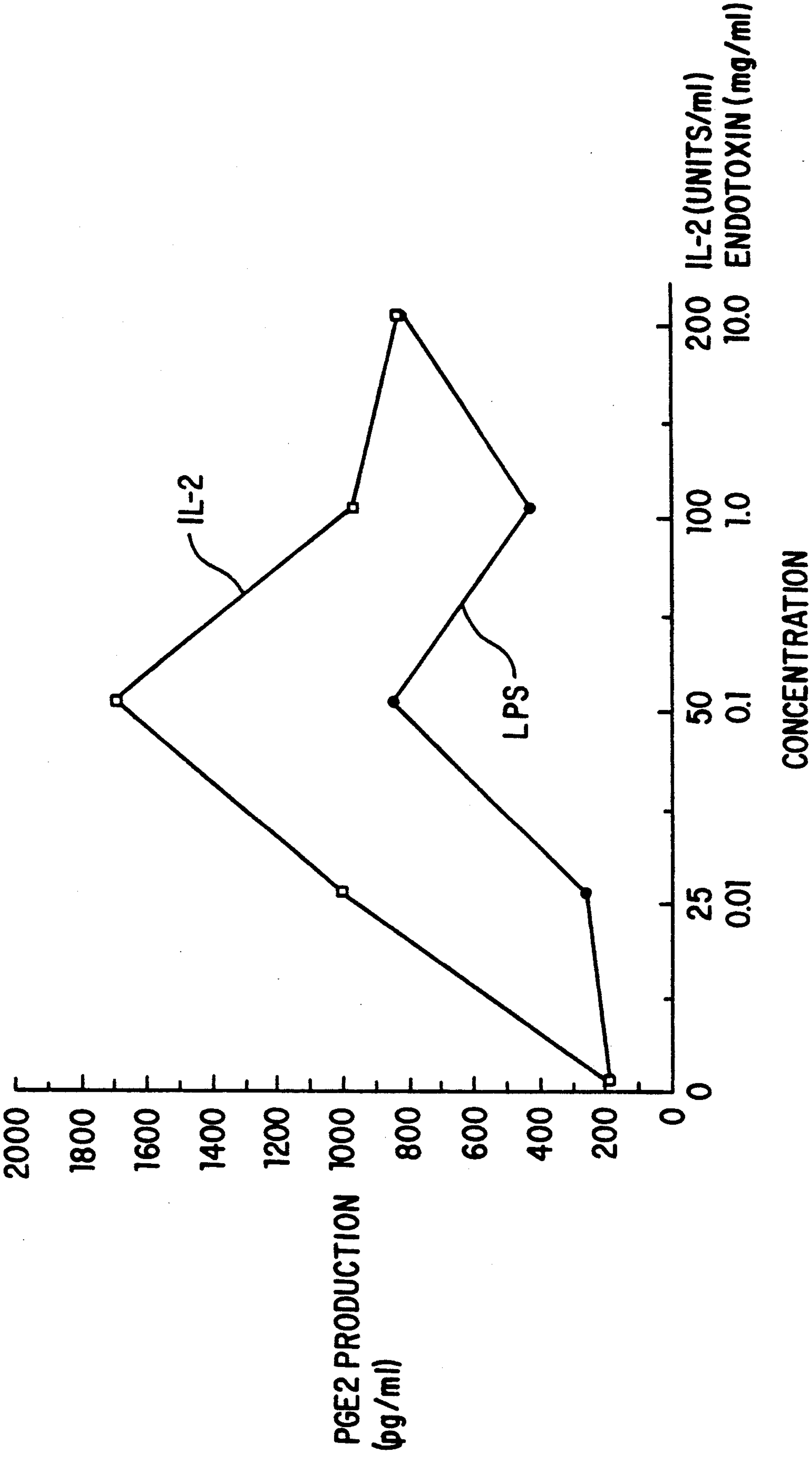
FIG. 9. PGE2 production in response to endotoxin or IL2. C3H/HeJ adherent spleen cell production of PGE2 in response to increasing doses of endotoxin or IL2 is shown.

Baseline PGE2 production by SAC was 180 pg/ml. Each concentration of endotoxin stimulated PGE2 production (range 260–880 pg/ml) (FIG. 9). Similarly, each concentration of IL2 tested increased PGE2 production. With both stimulants, PGE2 production peaked at intermediate doses and then declined, apparently due to toxicity to the adherent cells.

IL2 Inhibits LPS-Induced PGE2 in C3H/HeJ SAC

Figure 10:
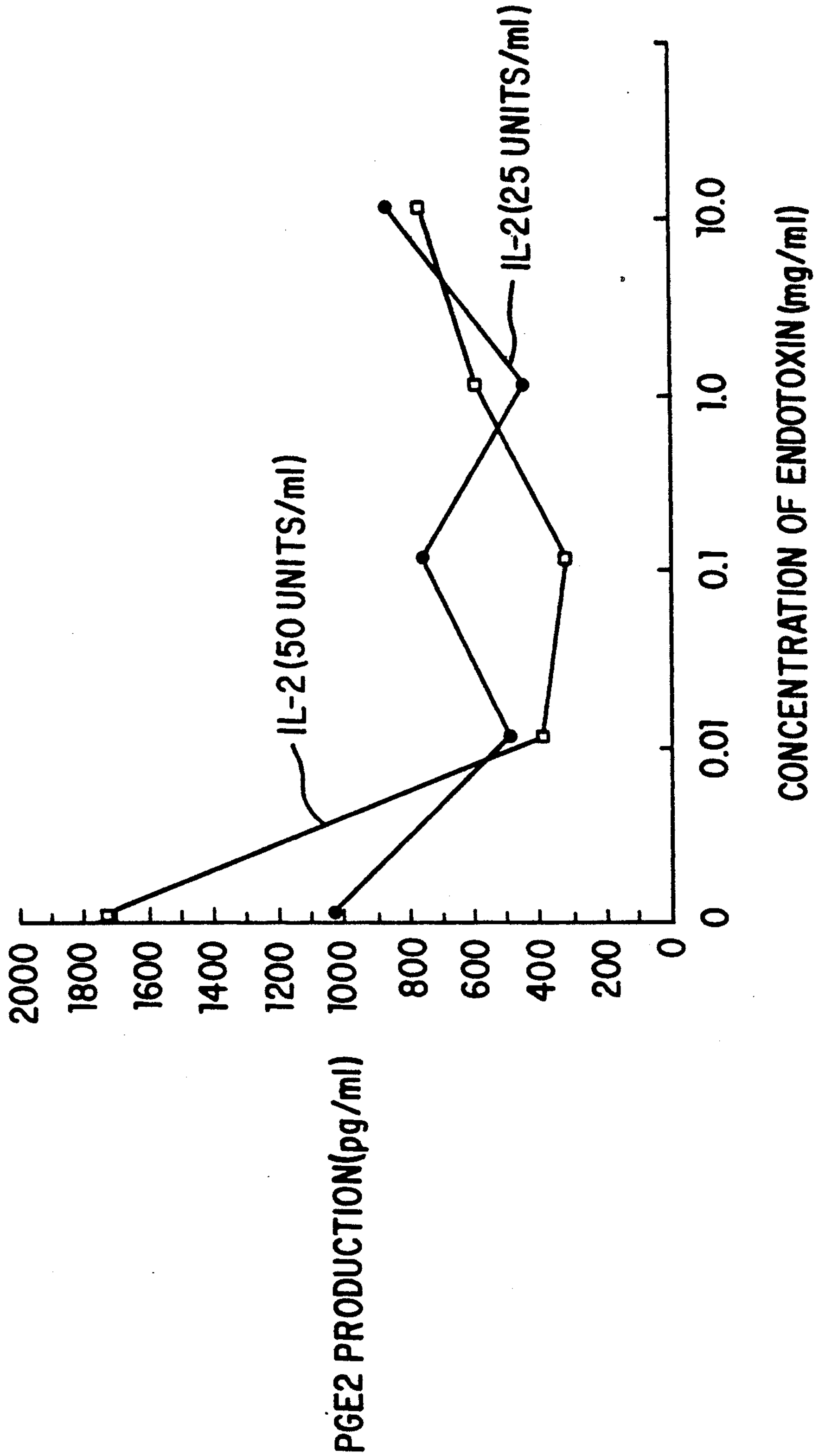
FIG. 10. Effect of IL2 on endotoxin-induced PGE2 production by murine adherent cells. Production of PGE2 by C3H/HeJ adherent spleen cells is shown in response to increasing concentrations of IL2 alone (0 LPS) or in the presence of 0.01 or 1 mg/ml endotoxin.

Low concentrations of IL2 (25 and 50 u/ml) inhibited the expected increased in PGE2 production in response to endotoxin. In the presence of IL2, increasing LPS concentrations were unable to stimulate PGE2 production above the "IL2-only" background (FIG. 10).

Figure 11:
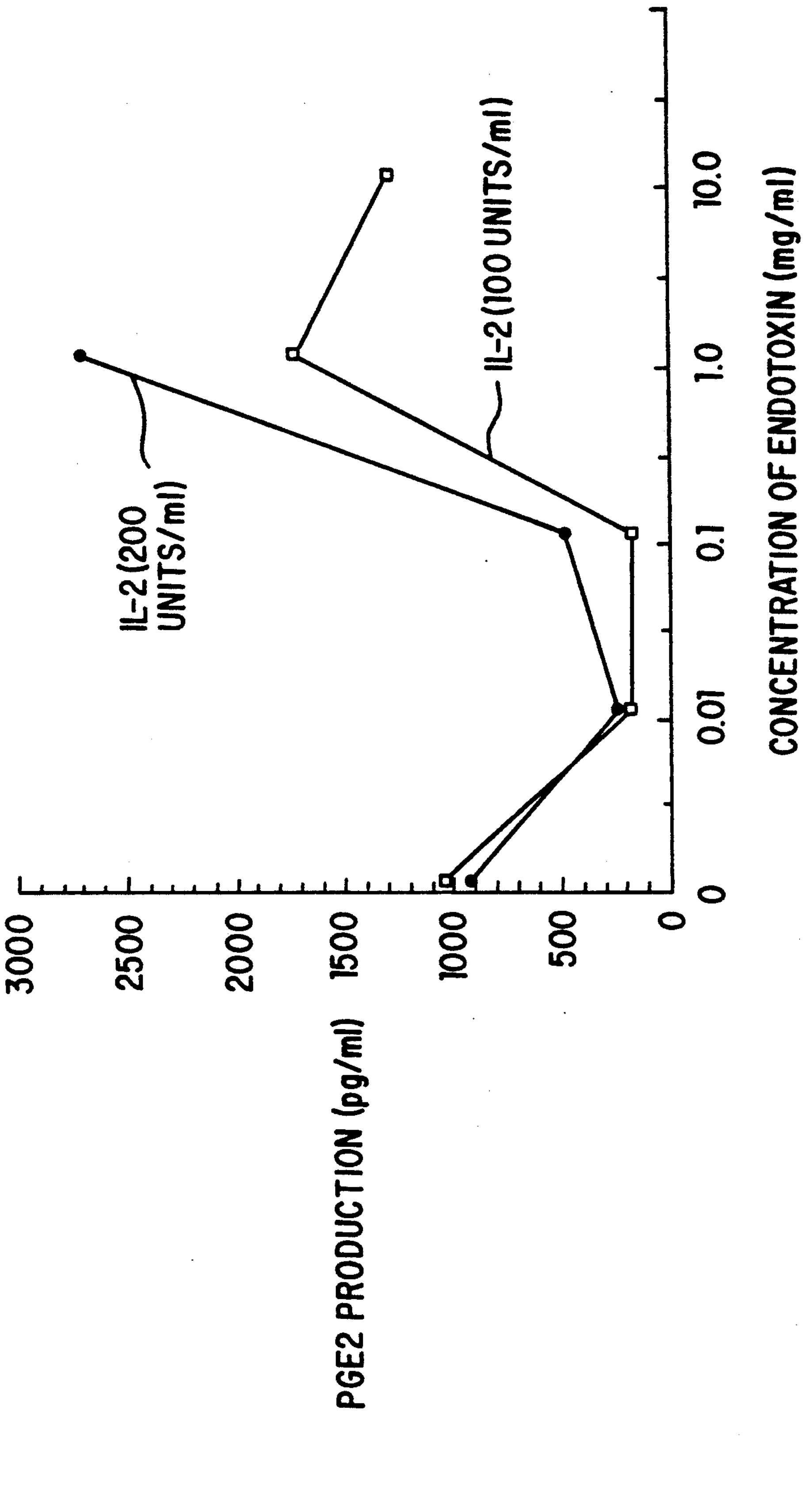
FIG. 11. Effect of high concentrations of IL2 on endotoxin-induced PGE2 production by murine adherent cells. PGE2 production by C3H/HeJ adherent spleen cells in response to increasing concentrations of endotoxin in the presence of 25 or 50 units/ml (~3.3 or 6.6 ng/ml) IL2 is shown.

When higher concentrations of IL2 (100 and 200 u/ml) were used, PGE2 production was stimulated to endotoxin concentrations above 0.1 mg/ml (FIG. 11).

Endotoxin Inhibits (IL2-Induced PGE2 in C3H/HeJ SAC

Figure 12:
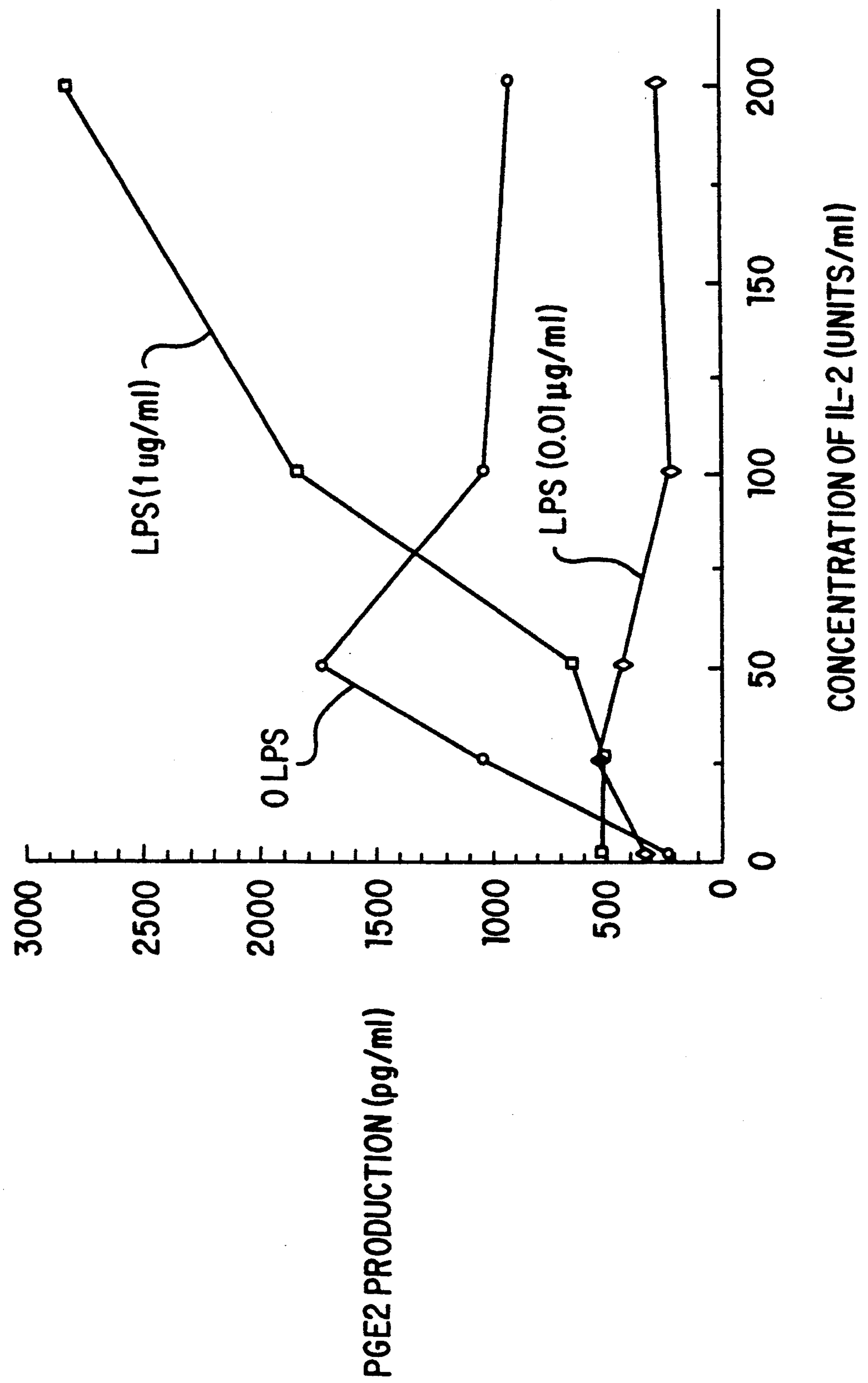
FIG. 12. Effect of endotoxin on IL2-induced PGE2 production by murine adherent cells. PGE2 production by C3H/HeJ adherent spleen cells in response to increasing concentrations of endotoxin in the presence of 100 or 200 units/ml (~13.3 or 26.6 ng/ml) IL2 is shown.

A low concentration of endotoxin (0.01 mg/ml) inhibited the expected increase in PGE2 production in response to IL2 (FIG. 12) This inhibitory effect was also evident with 0.1 mg/ml endotoxin. In contrast, a higher concentration of endotoxin (1 mg/ml) enhanced PGE2 production stimulated by higher concentrations of IL2 (100 and 200 u/ml (FIG. 12).

C. DISCUSSION

The resistance of endotoxin-hyporesponse C3H/HeJ mice to LPS-induced mortality was overridden by higher doses. IL2 could also be lethal in this mouse strain, more so than in endotoxin-sensitive A/J mice. The nature of the lethal effects of IL2 resembled that normally associated with endotoxin. First, fractionated sublethal doses resulted in higher mortality rates than did a single dose, similar to the sensitization phenomenon observed with endotoxin administration. Furthermore, a known endotoxin inhibiting agent, polymyxin B (Bannatyne, R. M. et al., *J. infec. Dis.* 136:469–473 (1977), prevented IL2-induced death. In addition to its endotoxin binding and inhibiting activity, polymyxin may bind to endotoxin receptors on cells (Bannatyne et al., supra). These results therefore raise the possibility that both IL2 and endotoxin share a monocyte activation pathway.

This notion received support from the in vitro observations that both IL2 and endotoxin stimulated adherent cell (presumably macrophage or monocyte) PGE2 production (FIG. 9), and the two agents could cross-inhibit. These findings strongly suggest competitive inhibition at a common receptor between endotoxin and IL2. The stimulatory effects of the particular endotoxin preparation used here, which is relatively high in protein content, is thought to be mediated by activation of LAP-binding the portion of the endotoxin receptor (Doe, W. F. et al., *J. Immunol.* 123:2304–2310 (1979)), since the lipid A-binding portion of the endotoxin receptor is not expressed in C3H/HeJ cells. Therefore competitive binding of endotoxin and IL2 would be postulated to occur at the LAP-binding subunit, a site less potent than the Lipid A binding site or the "complete" Lipid A+LAP site.

The observation that polymyxin inhibited IL2-induced mortality can be explained by competitive binding of polymyxin to the endotoxin receptor, preventing IL2 from inducing monocyte activation. This is supported by the demonstration that (i) polymyxin induces TNF production by human monocytes; (ii) polymyxin limits monocyte TNF responses to both endotoxin and IL2; and (iii) IL2 and endotoxin cross-inhibit the stimulation of human monocyte TNF responses (see Example III, above).

The common pathway proposed here for IL2 and endotoxin action on cells of the monocyte/macrophage lineage can explain why high doses of IL2, as currently used in the anti-tumor therapy, produce toxic effects similar to those produced by endotoxin infusion, which are often associated with increased levels of circulating monocyte-derived TNF (Michie, H. R. et al., *Ann. Surg.* 4:493-503 (1988). Such high doses of IL2 would be expected to overstimulate monokine release resulting in significant metabolic and neurohormonal derangements.

A unifying model proposed here postulates the following series of events: Endotoxin stimulates monocytes to produce IL1, which, in turn stimulates T cells to produce IL2. The monocyte LAP receptors can bind this newly produced IL2, resulting in minimal monocyte activation. However, when bound to the LAP receptor, IL2 prevents endotoxin (comprising both lipid A and LAP) from achieving maximal monocyte activation. Depending on the rate of IL2 production and its available concentration, further endotoxin molecules would find the receptor occupied or available. This may explain why endotoxin sensitization requires short intervals between successive doses whereas de-sensitization requires longer intervals.

The ability of exogenously added IL2 to inhibit endotoxin-stimulated TNF production (as shown in Example III, above) can be explained by IL2 binding to the LAP receptor and blocking maximum TNF stimulation by endotoxin. This may also explain why patients producing "normal" amounts of IL2 appear to fare better after endotoxin-associated critical illness, such as trauma, burns, and sepsis than patients showing an IL2 deficiency.

It is therefore proposed that therapy with low doses of IL2, aimed at restoration of adequate levels, will prevent excessive and unwanted metabolic responses to endotoxemia via inhibition at the level of the monocyte/macrophage. In contrast to the various untoward effects of high-dose IL2 therapy, a low dose regimen aimed at IL2 "normalization" is unlikely to stimulate or maintain the expression of IL2 receptors on monocytes, T cells, or other sites. Such low doses of IL2 are unlikely to lead to problems with immune complexes, since antibodies produced in response to IL2 appear to be of a non-neutralizing variety. With such low dose therapy, any signs of toxicity or evidence of monocyte activation could serve as an efficient indicator for dosage alteration.

EXAMPLE VI

In Vitro Modulation by IL2 of the Uptake of Endotoxin by Human Monocytes

The following data, from a series of experiments performed on blood from a healthy human donor, demonstrate that IL2 modulates the uptake of endotoxin by human monocytes.

A. MATERIALS AND METHODS subject

To demonstrate the effect of IL2 on human monocyte uptake of endotoxin, a series of experiments were performed on blood from a healthy human donor.

On separate days, 100-150 mls of citrated blood was drawn and separated by ficoll density centrifugation to yield peripheral blood mononuclear cells (as previously described).

Isolation of Monocyte Populations

To isolate monocyte populations, equal aliquots of PBMC were allowed to adhere in plastic culture plates (96 well plates were used in initial experiments, 16 well plates were used in later experiments) for 3 successive 30 minute periods at 37 degrees centigrade and 5% $CO_2$. Nonadherent cells were washed free with media (RPMI 1640 with added glutamine as before) between successive adherent stages. Under microscopy, adherent cells were then accessed for uniformity and viability. The aim was to obtain an equal number of cells in each experiment, in the range of 5,000 to 200,000, of monocytes per well.

Treatment of Adherent Cells

Adherent cells were then exposed to concentrations of sterile, recombinant IL2 (Boehringer, diluted with media from 10,000 units/ml to appropriate concentrations) for periods of 15 minutes (initially in FIG. 13A-13C but for periods of 5 minutes in FIGS. 14A-18) under the above culture conditions. Following this exposure to IL2, concentrations of radiolabelled endotoxin (*E. coli* 055-B5 Bovine extracted LPS, Sigma Chemical Co., 60 mg, exposed to an atmosphere of Tritium gas for 14 days at room temperature in water resulting in 340.00 mCi of tritium, Dupont NEN laboratories, Boston, USA) were added to adherent cells and IL2, for a further 5 minutes incubation.

At the end of these exposures, supernatants were vigorously decanted and the cells were washed three times with media.

For the initial experiment, adherent cells were raised by meticulous scraping with a "rubber policeman". In subsequent experiments recovery was obtained by incubating adherent cells with sterile 0.5% lidocaine for 15 minutes, followed by the addition of sterile water to raise and rupture adherent cells. The resulting fluid was then brought to 5 mls with liquid scintillation fluid and counted in a Beta counter to measure incorporation of Tritiated endotoxin.

The methods of the initial experiments were refined, as above, to yield repeatable dose response curves for radiolabelled LPS incorporation and to retrieve as many monocytes as possible.

In all experiments, duplicate or triplicate samples were used to assess labelling of adherent monocytes in response to endotoxin. Where possible, duplicate or triplicate samples were also used to estimate the effect of preincubation with IL2 on LPS uptake.

The results are illustrated graphically in FIGS. 13A-21.

Figure 16:
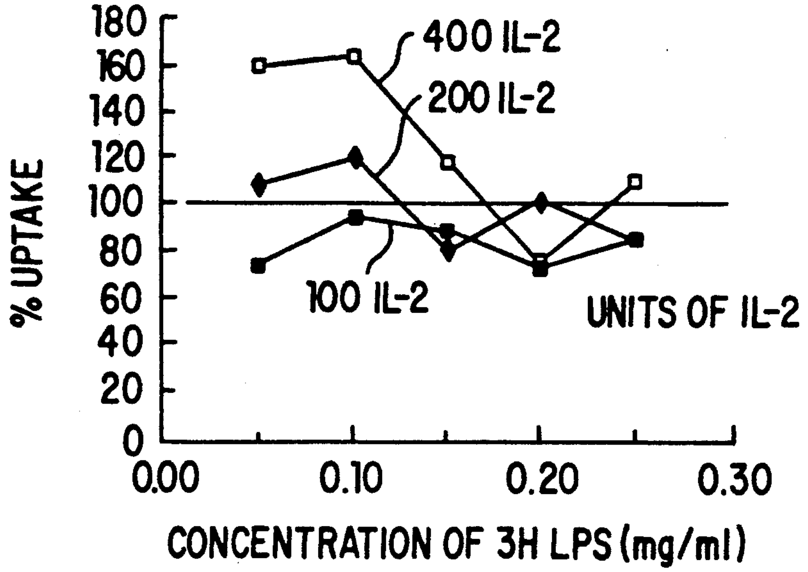
FIG. 16. Variable effect of IL2 concentrations of 100 or more units/ml on uptake of labeled LPS by monocytes.
Figure 17:
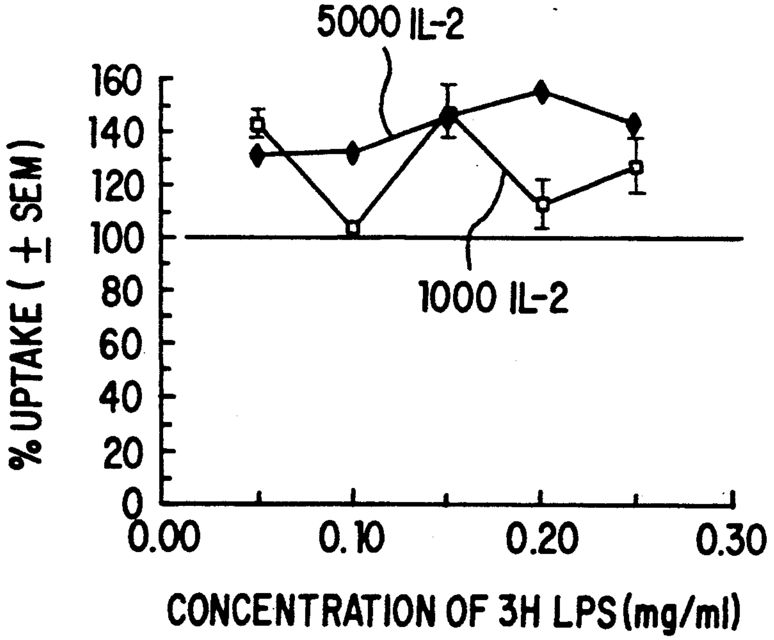
FIG. 17. Effect of IL2 concentrations of 1,000 and 5,000 units/ml to increase the uptake of labeled LPS by monocytes.
Figure 18:
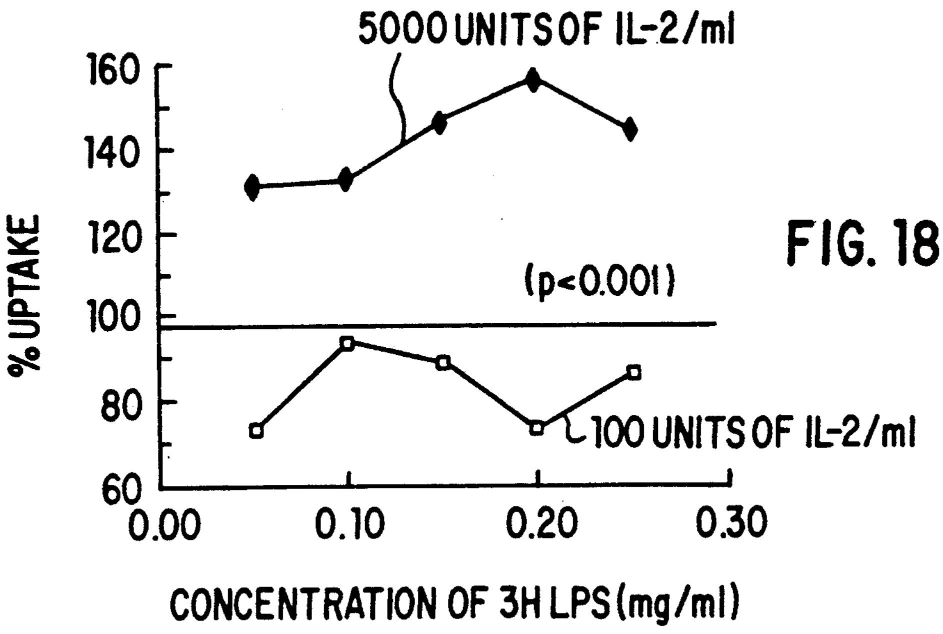
FIG. 18. Stimulatory effect of IL2 at 5,000 units/ml and the inhibitory effect of IL2 at 100 units/ml on monocyte uptake of labeled LPS.
Figure 19:
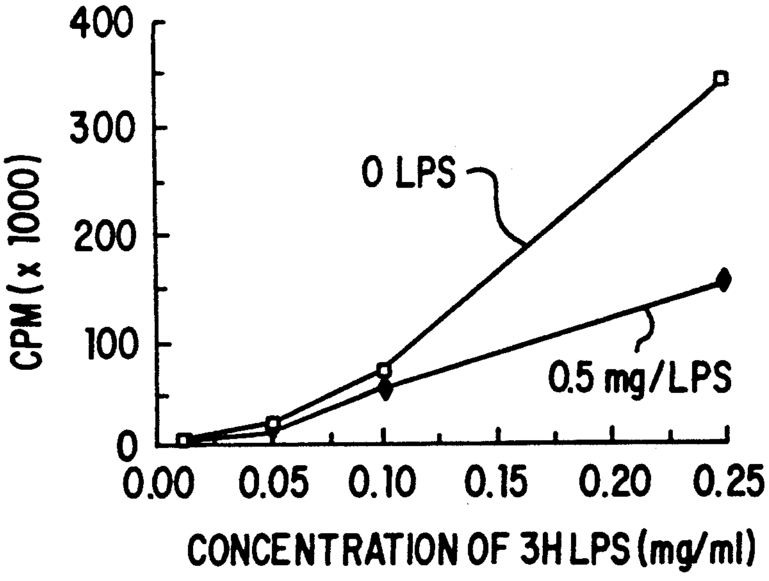
FIG. 19. Inhibitory effect by cold (unlabeled) LPS on the uptake of tritium-labeled LPS by monocytes.
Figure 20:
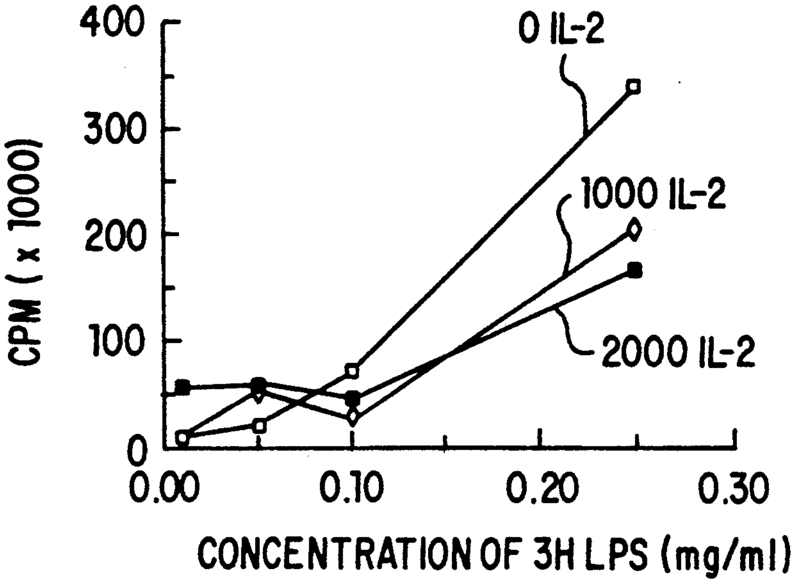
FIG. 20. Inhibition by IL2 at 1,000 and 2,000 units/ml of the uptake of tritium-labeled LPS by monocytes.
Figure 21:
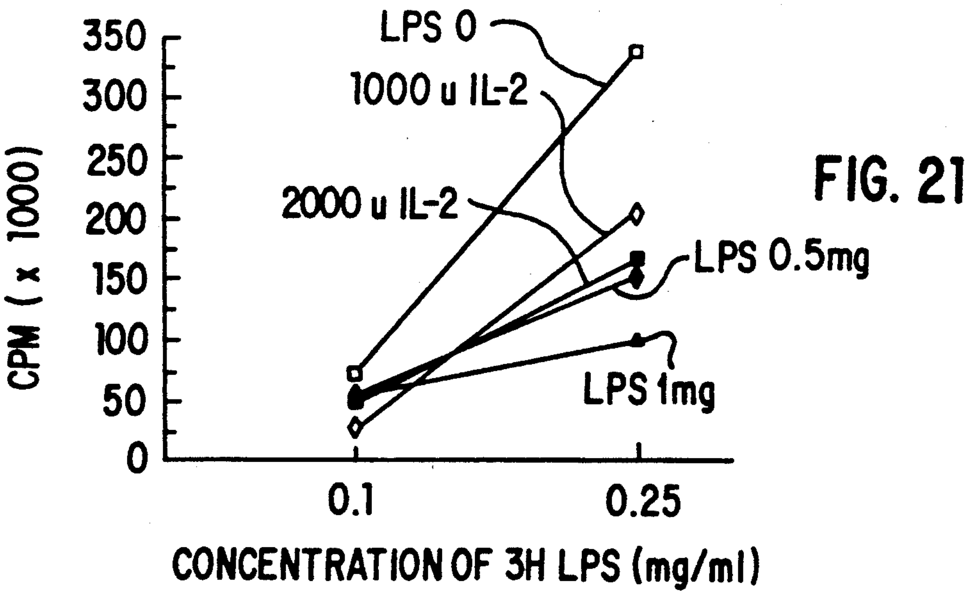
FIG. 21. Inhibition by LPS or IL2 of tritium-labeled LPS uptake by monocytes.

The experiment illustrated in FIGS. 19-21 was performed as just described with the following two exceptions. First, cells were adhered at 200 ul of PBMC (mononuclear cells) at $5\times10^6$/ml, i.e. about 100 times greater than in the initial experiments (FIG. 13A-13C') and 10 times higher than later experiments (FIGS. 16-18). Second, exposure time to hot LPS (3H LPS) was 3 minutes compared to 5 and 15 minutes in earlier experiments.

Statistics

In all cases, dose response curves are given for means of at least duplicate samples. Standard errors are also given, but due to their small size may not be evident on all dose response curves.

B. RESULTS

Uptake of Labelled LPS by Monocytes

The regular dose response (FIGS. 13A, 13B and 13C) and log dose response curves (FIGS. 13A', 13B' and 13C') demonstrate that LPS was taken up by monocytes in a regular, repeatable fashion.

Preincubation of Monocytes with IL2, or LPS Prior to Exposure to LPS

In all cases, dose response curves for labelled LPS uptake were altered when IL2 was present in the culture (FIGS. 15A to 18, 20 and 21).

Figure 14A:
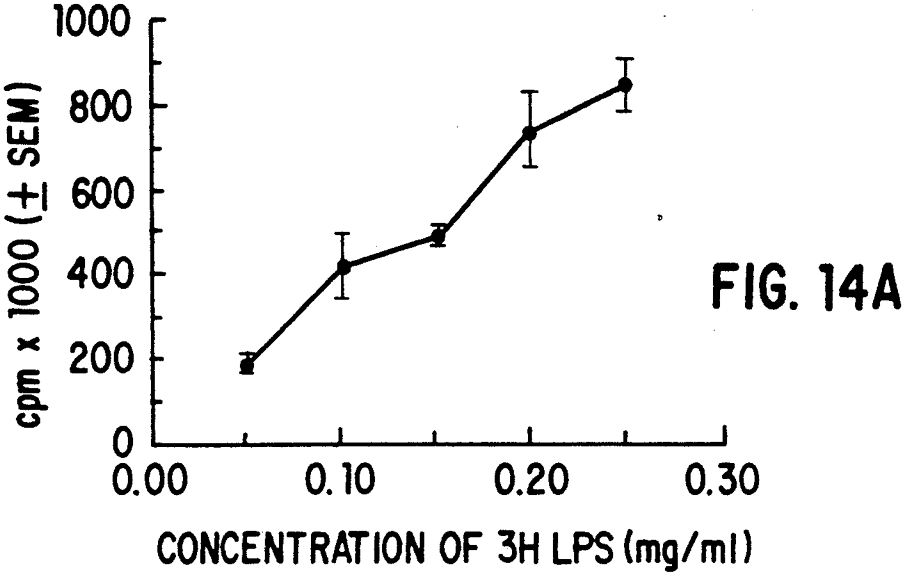
FIG. 14A and 14B. The uptake of tritium by monocytes was measured in the presence of concentrations of endotoxin between 0.05 and 0.25 mg/ml.
Figure 14B:
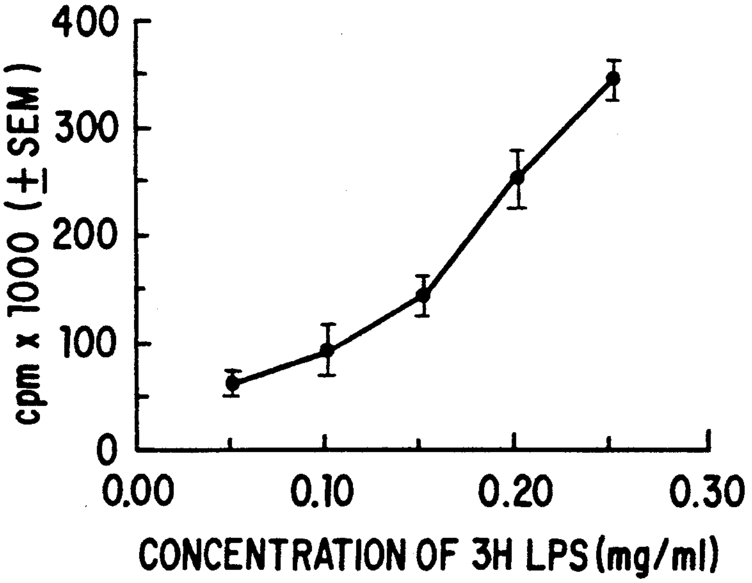

In FIGS. 14A and 14B the incorporation of tritium was measured in the presence of concentrations of endotoxin between 0.05 and 0.25 mg/ml.

Figure 15A:
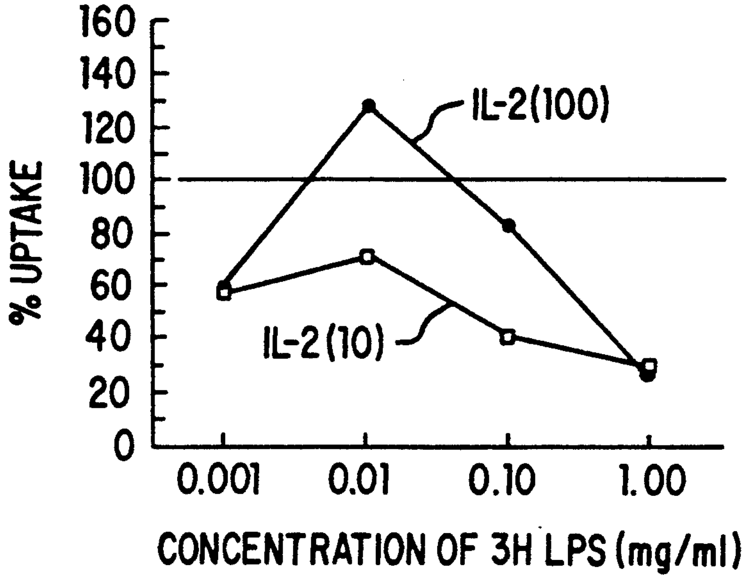
FIG. 15A–15D. Inhibition by IL2 of LPS uptake by monocytes.
Figure 15B:
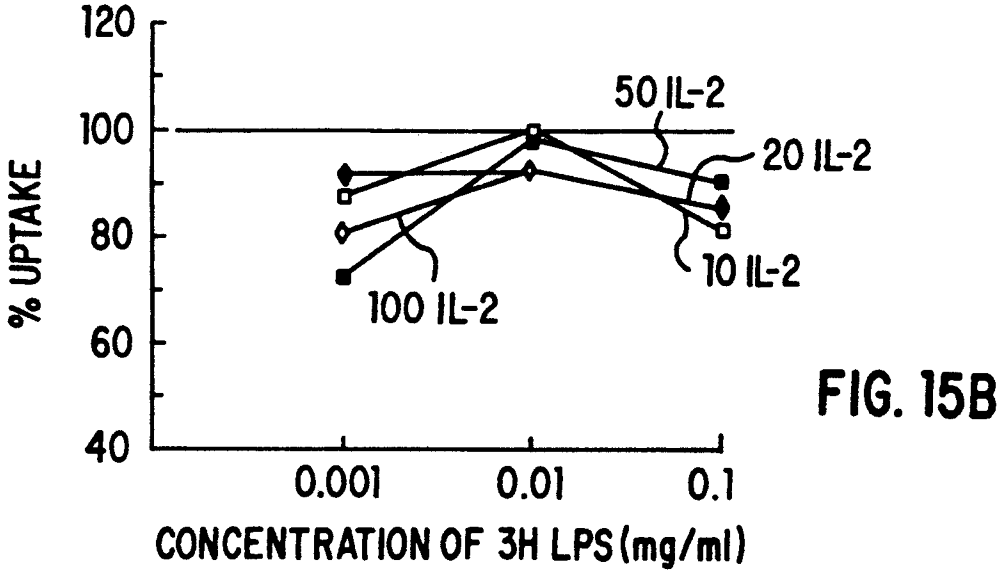
Figure 15C:
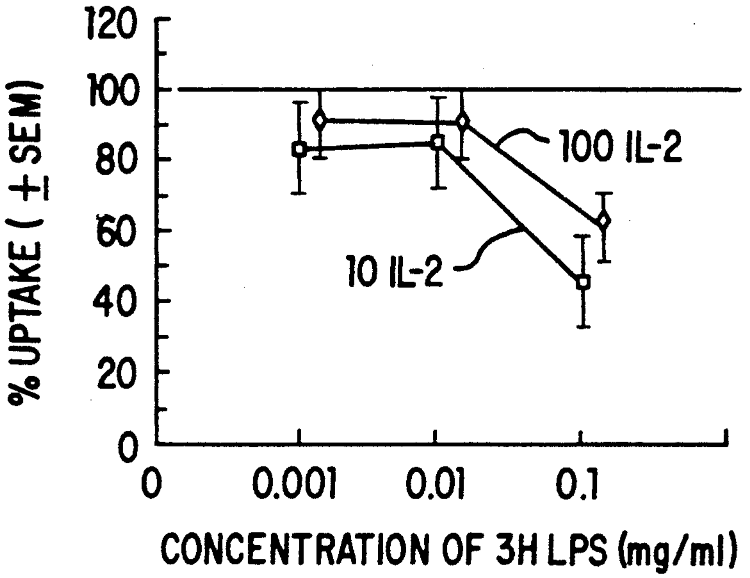
Figure 15D:
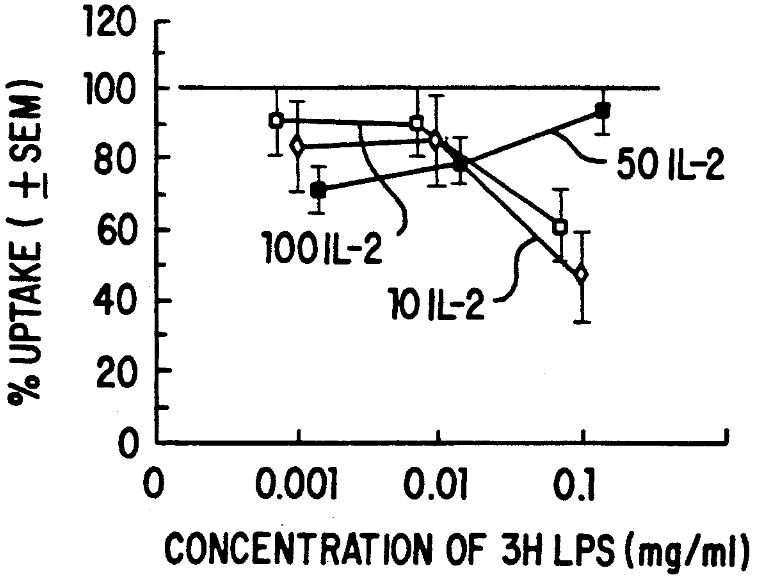

IL2 concentrations of 100 units/ml or less inhibited the uptake of LPS by monocytes (FIGS. 15A–15D). FIGS. 15C and 15D are a compilation of available data for the effect of IL2 (10, 50 and 100 units of IL2). (The data for FIGS. 15A, B, C and D were obtained on the same day as the data in FIGS. 13 and 14.)

In FIGS. 15A–18, the percentage binding, i.e., the ratio of cpm obtained in the presence of IL2 and labelled LPS/the cpm obtained with radiolabelled LPS alone, is plotted for various concentrations of IL2 in response to increasing concentrations of radiolabelled LPS.

IL2 concentrations of 100, 200 and 400 units/ml had a variable effect on the uptake of labelled LPS by monocytes (FIG. 16). (The data were obtained on the same day as the data in FIG. 14A).

High concentrations of IL2 (1000 and 5000 units/ml) increased the uptake of labelled LPS by monocytes (FIG. 17). (The data were obtained on the same day as the data in FIG. 14B).

FIG. 18 demonstrates the stimulatory effect of IL2 at 5000 units/ml and the inhibitory effect of IL2 at 100 units/ml on monocyte uptake of labelled LPS.

FIG. 19 illustrates the inhibition of uptake of 3H LPS by monocytes by cold (unlabelled) LPS at 0.5 mg/ml.

FIG. 20 illustrates the inhibition of uptake of 3H LPS by monocytes by 1,000 and 2,000 units/ml of IL2.

FIG. 21 illustrates the inhibition of 3H LPS uptake by monocytes by LPS (0.5 and 1 mg/ml) or IL2 (1,000 and 2,000 U/ml). When expressed in terms of units of IL2 per cell number, these data would be approximately equivalent to 100 units per ml of culture. Therefore, these data (1,000 and 2,000 units of IL2 per ml, and per $5\times10^6$ PBMC cells/ml) are equivalent to 10 and 20 units per ml in FIG. 13A–13C', as cells were adhered at $7\times10^4$/ml in the earlier experiments. Due to the high volume of blood required (150 mls) for this latest experiment, it was not possible to perform duplicate tests.

C. DISCUSSION

Figure 13A:
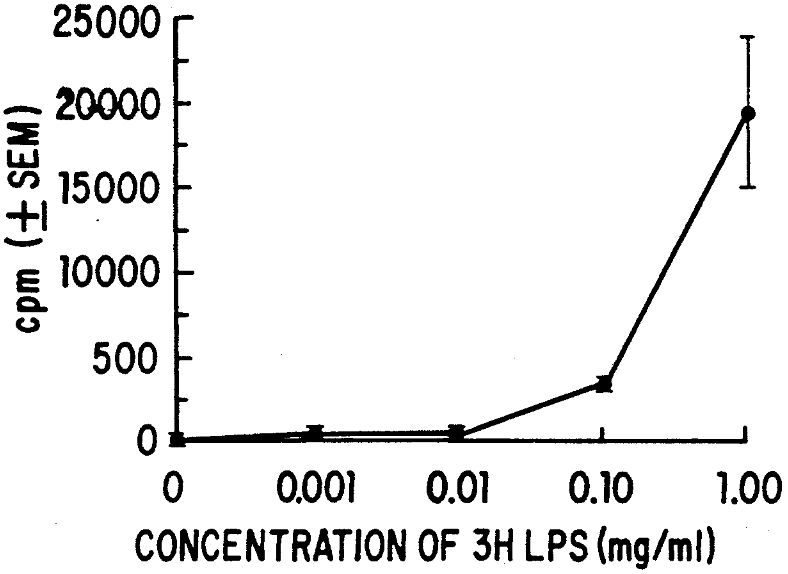
FIG. 13A–13C'. Uptake of LPS by monocytes.
Figure 13A:
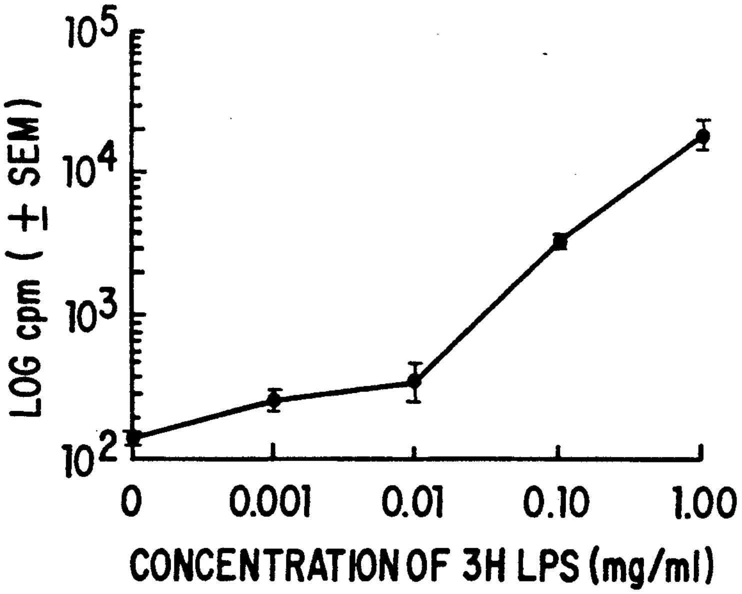
Figure 13B:
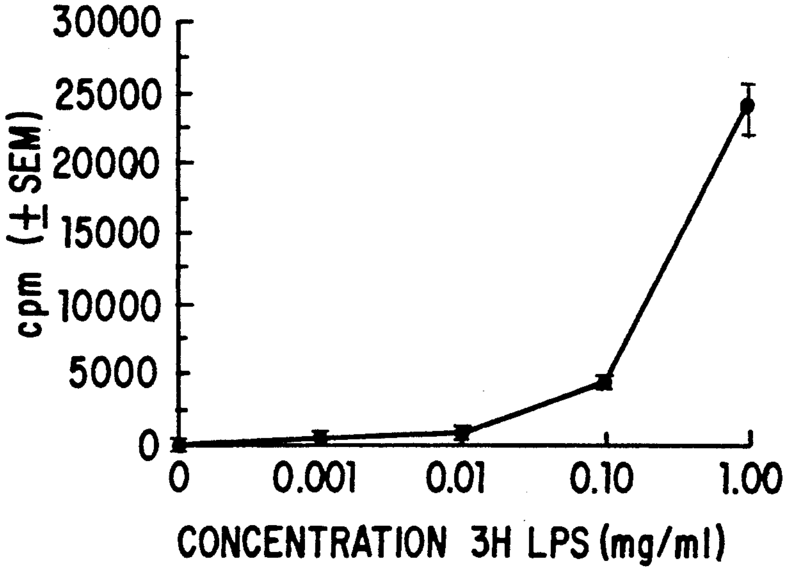
Figure 13B:
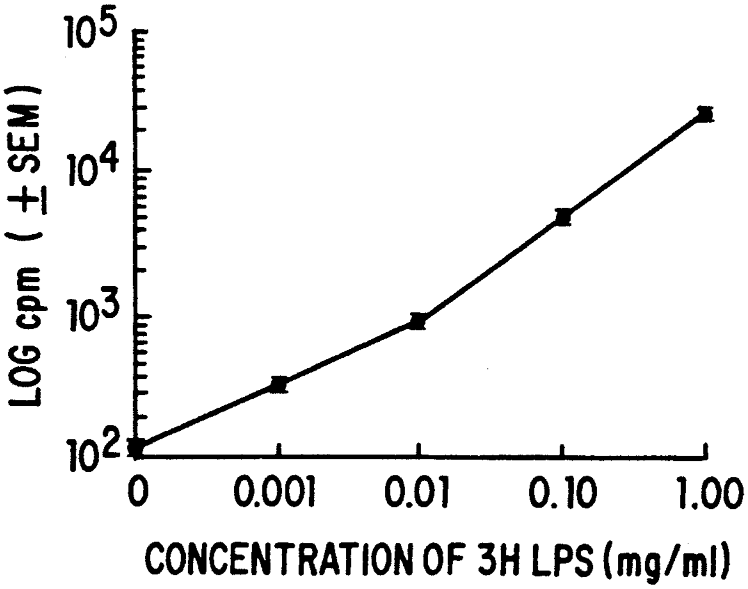
Figure 13C:
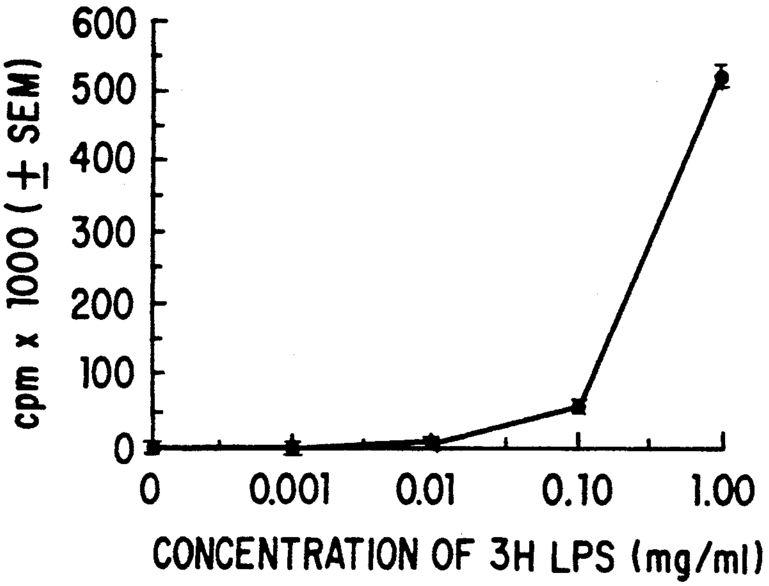
Figure 13C:
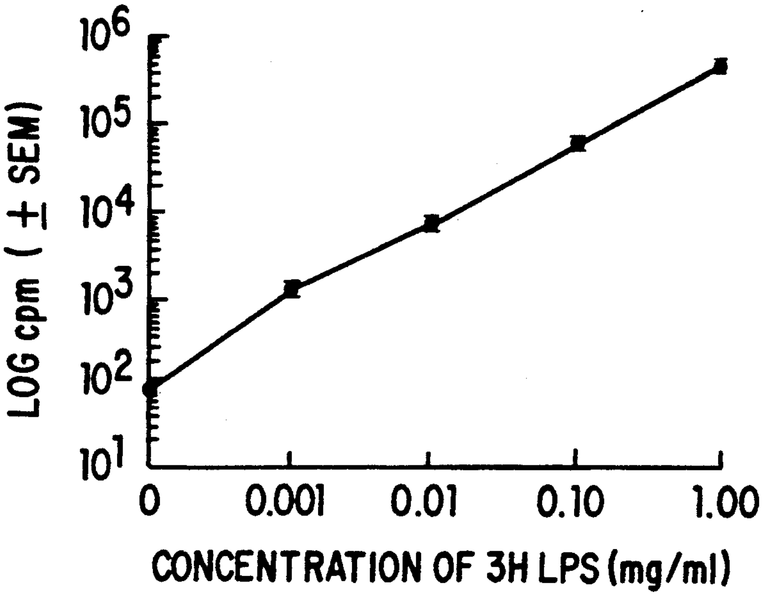

Applicant's previous work demonstrated that IL2 modifies the response of monocytes to endotoxin. FIGS. 13A–13C demonstrate that LPS was taken up by monocytes in a regular repeatable fashion. Although it was not determined whether LPS was adsorbed onto the monocyte membrane or quickly internalized into the monocyte cytoplasm, the term "uptake" will be used when describing this process without implying a mechanism by which it occurs. This uptake proceeded in a regular fashion.

Preincubation of monocytes with IL2 prior to exposure to LPS altered dose response curves for labelled LPS uptake (FIGS. 15A to 18, 20 and 21).

The mode of interference of IL2 with the uptake of LPS by monocytes followed a pattern. For concentrations of 100 units/ml or less, IL2 inhibited the uptake of LPS by monocytes (FIGS. 15A, 15B, 15C, and 15D). IL2 concentrations of 200 to 400 units had a variable effect, either leaving unaltered or inhibiting the binding of high LPS concentrations while augmenting the uptake of low concentrations of LPS (FIG. 16). High concentrations of IL2 (1,000 and 5,000 units/ml) consistently increased the uptake of LPS by monocytes (FIGS. 17 and 18).

These data further demonstrate that IL2 regulates the immune response in humans and, in particular, monocyte activation in response to endotoxin. The ability of low concentrations of IL2 to down-regulate the uptake of LPS by monocytes supports the view that endogenous or exogenous IL2 will be a useful adjunct in the therapy of those patients in whom excessive monokine production is causing an ongoing metabolic disturbance. The data which show that high concentrations of IL2 appear to increase the uptake of LPS might explain why those patients in protocols in which high dose IL2 therapy is targeted against tumours (Rosenberg et al., New Eng. J. Med. 313:1485–1490 (1985)) suffer effects similar to endotoxin infusion (Michie et al., Annals Surg. 208:493–503 (1988). In addition, it supports the idea that IL2 provides a facility for both the up-regulation and down-regulation of the immune response.

The concentrations of IL2 (10, 50 and 100 units/ml) which reduced the uptake of LPS in these experiments were the same concentrations which reduced human PBMC TNF production, human monocyte TNF production, and the production of PGE2 by C3H/HeJ mice in previous experiments.

The latest experiments were performed on blood from a normal healthy individual, who has been tested on numerous occasions as a control in various experiments and been shown to secrete normal quantities of IL2 and a minimal amount of TNF in response to endotoxin.

In summary, these data provide evidence for the interaction of IL2 on monocyte endotoxin receptor activity and demonstrate that IL2 plays a role in modulating the human response to endotoxaemia which is frequently present in patients with cancer, surgery, trauma, sepsis or even occasionally in otherwise healthy subjects.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains an as may be applied to the essential features hereinbefore set forth as follows in the scope of the appended claims.

What is claimed is:

1. A method of treating cachexia in an animal comprising administering to said animal a therapeutically effective amount of interleukin 2 or a functional analogue thereof which retains the characteristics of interleukin 2.

2. The method of claim 1, wherein said interleukin 2 is human interleukin 2.

3. The method of claim 2, wherein said human interleukin 2 is produced by using recombinant DNA technology.

4. The method of claim 1, wherein said effective amount of interleukin 2 is between 50 and 5000 units/kg body weight.

5. The method of claim 1, wherein said effective amount of interleukin 2 is between 100 and 500 units/kg body weight.

6. The method of any of claims 1, 2, 3, 4 or 5 wherein said interleukin-2 is administered subcutaneously, transdermally, intravenously, orally, intranasally, intramuscularly, intraperitoneally, bucally, or rectally.

7. The method of claim 1, wherein said cachexia occurs substantially associated with cancer.

8. The method of claim 1, wherein said cachexia occurs substantially associated with bacterial infection.

9. The method of claim 1, wherein said cachexia occurs substantially associated with sepsis.

10. The method of claim 1, wherein said cachexia occurs substantially associated with parasitic infection.

11. The method of claim 1, wherein said cachexia occurs substantially associated with viral infection.

12. The method of claim 11, wherein said viral infection is with human immunodeficiency virus 1.

13. The method of claim 1, wherein said cachexia occurs substantially associated with a catabolic disorder.

14. The method of claim 13, wherein said catabolic disorder is a result of surgery, sepsis, burn injuries, calorie deprivation, chemotherapy, radiation therapy, uncontrolled diabetes, or traumatic injury.

15. A method of treating symptoms substantially associated with excessive monocyte stimulation caused by endotoxin in an animal, comprising administering to said animal a therapeutically effective amount of interleukin 2 or a functional analogue thereof which retains the characteristics of interleukin 2.

16. The method of claim 15, wherein said effective amount of interleukin 2 is between 50 and 5000 units/kg body weight.

17. The method of claim 15, wherein said effective amount of interleukin 2 is between 100 and 500 units/kg body weight.

18. The method of claim 15, wherein said interleukin 2 is administered subcutaneously, transdermally, intravenously, orally, intranasally, bucally, intramuscularly, intraperitoneally, or rectally.

19. The method of claim 15, wherein said symptoms are substantially associated with adult respiratory distress syndrome or renal failure in a critical illness.

20. The method of either claim 1 or 15, wherein said animal is a human.

* * * * *